US006631647B2

(12) United States Patent
Seale

(10) Patent No.: US 6,631,647 B2
(45) Date of Patent: Oct. 14, 2003

(54) SYSTEM AND METHOD FOR QUANTIFYING MATERIAL PROPERTIES

(76) Inventor: Joseph B. Seale, 98 Day Rd., Gorham, ME (US) 04038

( * ) Notice: Subject to any disclaimer, the term of this patent is extended or adjusted under 35 U.S.C. 154(b) by 0 days.

(21) Appl. No.: 10/133,187

(22) Filed: Apr. 26, 2002

(65) Prior Publication Data

US 2002/0157478 A1 Oct. 31, 2002

Related U.S. Application Data

(60) Provisional application No. 60/286,510, filed on Apr. 26, 2001.

(51) Int. Cl.[7] ............................................. G01D 1/16
(52) U.S. Cl. ........................................... 73/789; 73/760
(58) Field of Search .................... 73/760, 789; 700/44; 702/33, 42, 43, 130

(56) References Cited

U.S. PATENT DOCUMENTS

| | | | |
|---|---|---|---|
| 4,074,569 A | 2/1978 | Sambrook | 73/94 |
| 4,238,952 A | 12/1980 | Koopmann | 73/15.6 |
| 4,383,450 A | 5/1983 | Pringiers | 73/790 |
| 4,658,362 A * | 4/1987 | Bhatt | 700/145 |
| 5,092,179 A | 3/1992 | Ferguson | 73/790 |
| 5,933,345 A * | 8/1999 | Martin et al. | 700/44 |
| 6,332,364 B1 | 12/2001 | Buschmann | 73/788 |
| 6,487,459 B1 * | 11/2002 | Martin et al. | 700/44 |

* cited by examiner

Primary Examiner—Edward Lefkowitz
Assistant Examiner—Andre Allen
(74) Attorney, Agent, or Firm—Nils Peter Mickelson

(57) ABSTRACT

A materials characterization method models dynamic, non-linear, temperature-dependent stress, strain, hysteresis, creep, and loss of elasticity at high strain, both in test samples and in Finite Element Analysis (FEA). Incorporating universal properties of statistical mechanics and adapting domain models from ferromagnetics to the higher-dimensional realm of stress tensors, the model is applicable to polymers, rubbers, liquids, and metals in elastic and plastic deformation. The model quantifies the dynamics of both plastic and brittle failure. Apparatus and methods are shown for testing material samples and matching the computational model to sample characteristics, leading to a set of characterizing parameters and predictive simulations using those parameters. Though apparatus and testing protocols of the invention yield optimum characterizations, pre-existing data from conventional testing yield useful results.

15 Claims, 12 Drawing Sheets

SYSTEM AND METHOD FOR QUANTIFYING MATERIAL PROPERTIES

CROSS-REFERENCE TO RELATED APPLICATIONS

This application cliams benefit of Provisional Patent Application Ser. No. 60/286,510 filed on Apr. 26, 2001.

BACKGROUND OF THE INVENTION

Various tests have been used to characterize the mechanical properties of material samples, particularly of polymer plastics and elastomer or rubbery materials. In one short-term category are impact tests such as Izod impact, and Durometer testing. A thin piece of material is placed on a hard surface and impacted by a hard object at varying kinetic energies until permanent deformation or rupture is observed. Other hardness tests array materials according to which material will scratch which softer material, for example, diamond scratching sapphire, sapphire scratching quartz, etc. Creep properties are less often determined, since the testing is time-consuming. Samples may be subjected to a constant stress for an extended period at a controlled temperature while strain is measured, resulting in a graph of a time-dependent modulus of elasticity, the "creep modulus," representing the ratio of stress to strain plotted as a function of time. Since strain increases over time at constant stress due to material creep, the creep modulus is a decreasing function of time. Families of creep modulus graphs are typically plotted for selected fixed stresses and fixed temperatures. Creep modulus graphs commonly extend from a first measurement at one hour (of sustained stress) to 1000 hours or more. Each graph in a family of creep modulus graphs requires that a separate material sample be maintained at a separate temperature and stress in a test apparatus for the full duration, for example, 1000 hours, indicating the time-consuming and expensive nature of the testing. For testing of dynamic stress/strain relationships on an intermediate time scale between very short-term impact and very long-term creep, machines are sometimes employed that impose programmable progressively-increasing or cyclically-changing strain over time while measuring stress, typically over a time scale of seconds to minutes. Instron is a widely recognized manufacturer of devices for this kind of testing. Controlled strain is commonly applied to soft materials, especially elastomers, while stress is measured. On harder materials, where it can be difficult to control strain, stress is varied while strain is measured. In a common testing protocol, stress is increased monotonically while strain is measured. When a specified strain threshold is reached, typically where the material deviates from more or less reversible elastic behavior to plastic strain and permanent deformation, this threshold defines the yield stress. Complete failure or rupture of the sample defines ultimate stress, sometimes called tensile stress. In metals, material samples may be subjected to cyclic stress over millions of cycles at various stress levels, defining a fatigue stress threshold below which samples cease to exhibit progressive weakening or embrittlement leading to failure.

The traditional tests described above, usually not involving programmable test equipment, suffer from several limitations. The longer term tests involving sustained stresses at controlled temperature tie up equipment for long periods of time. Where process control is involved, the value of test data declines rapidly with the time it takes to obtain the data. While impact and scratch hardness types of tests provide quick results, tests for creep properties are far too slow to provide information for tuning real-time process parameters that produce the material. The short term tests measure only a failure threshold under a fixed set of conditions, providing little insight into other material properties. Combining test results can reveal material properties over wide-ranging conditions, but the results do not generate a predictive analytic model that could describe material response to a set of conditions outside the specific conditions of the test results. It would be desirable that test results could be used to define a predictive model of material properties, applicable to describing dynamic response of individual cells in a Finite Element Analysis, or FEA. Families of measured curves obtained under dynamic conditions and at varying temperatures provide a wealth of data that have not been reducible to a predictive model, even when the data span the conditions of concern for actual use of the material.

In U.S. Pat. No. 6,332,364 (2001), Buschmann et. al. describe a universal testing device capable of applying a programmable actuator for controlling a displacement imposed on a sample, a load cell for measuring the force associated with that displacement, data collection and signal conditioning apparatus, and control over humidity. Being programmable, this or a similar device can be made to test the stress response of a sample to an arbitrary time-varying strain. By appropriate feedback control to obtain a desired time-varying strain, such a device can be made to test the strain response for programmed time-varying stress. An earlier, simpler system is described by Sambrook et. al. in U.S. Pat. No. 4,074,569 (1978), where the device provides for preloading a sample, then causing the load to change abruptly to a fixed test load exceeding the preload, and then measuring a visco-elastic strain response to the test load over time. While Sambrook et. al. contemplate measurement of a time-dependent stress/strain relationship, and while Buschmann et. al. provide programmable actuation and sensing means that could potentially explore a complex, non-linear and time-dependent stress/strain dynamic, they provide no means for extracting meaningful simplifications or descriptive parameters from the multitude of testing possibilities. Sambrook et. al. further describe means for temperature control of the sample, recognizing that temperature is an important part of such a dynamic description, particularly in visco-elastic materials. Buschmann et. al. similarly recognize humidity as an important parameter.

The difficulty with conventional methods is the proliferation of possibilities for data collection over differing stresses, strains, temperatures, humidities, and the time-sequences involving these variables, without a method for reducing the data to a concise set of useful parameters. Such a method might appear to be provided by the teaching of Koopmann et. al. in U.S. Pat. No. 4,238,952 (1980), whose objective (from the Summary of the Invention) is "determining characteristic rheological quantities of viscoelastic materials, in particular rubber and rubber mixtures . . . . " Indeed, test data are boiled down to just two parameters, a viscosity and an elasticity, which are incorporated into a formula to describe stress/strain behavior. The method, however, is applicable only to a small class of rubbery substances, those soft enough to sustain an abrupt 60% compressive deformation without damage. One would desire some means for comparing viscoelastic properties over a wide range of materials spanning, for example, from latex rubber to hard neoprene rubber, and on to polypropylene, and on to polycarbonate. Lacking in the prior art is any integrated method of testing, data simplification, and predictive modeling of stress/strain behavior, applicable to a wide variety of materials under widely varying conditions of stress, time, and temperature.

As with nonlinear stress and strain in solids, a limited understanding of the dynamic properties of magnetic materials has limited the testing and characterization of these materials. Curve fitting techniques are used to capture initial magnetization curves of virgin samples, while coercive force and saturation values are used to approximate the character of a hysteresis loop at very high cyclic excitation, but the descriptors do not predict, for example, how small hysteresis loops behave for small cyclic excitations, with or without magnetic bias. In both solid mechanics and magnetics, very detailed models suffer from becoming too specialized, being applicable only to very particular materials under very particular conditions.

Better modeling, striking a compromise between true and accurate description on the one hand, and generality of application on the other hand, has the potential to lead to better testing, better quality control in manufacture and receiving, and better insight into how the materials behave and might be improved.

OBJECTS OF THE INVENTION

In light of the above-described limitations in material testing and characterization, it is one object to provide a dynamic software model by which the establishment of a small number of material parameters causes the model to predict strain when stress is varied dynamically or stress when strain is varied dynamically. A related object is that the software model predict how material response is affected by temperature. Another related object is that the software model take statistical account of the dynamics of multiple internal states of sub-microscopic components of a material whose properties are not uniform on a molecular scale. A further related object is that the statistical accounting include a model of energy transition domains, each one capable of occupying two or more semi-stable energy states at differing microscopic strain dislocations, with state transitions being promoted by thermal agitation and either promoted or inhibited by stress communicated from the surrounding material.

It is an object to provide an information processing system that calculates and adjusts material parameters of a dynamic stress/strain software model to obtain a best-fit match to data measured for a material sample, whereby these best-fit parameters characterize the sample and permit prediction of material stress/strain responses under variable simulated conditions, including conditions beyond or not produced in the testing phase. It is an object to provide means for bringing dynamic materials data to an information processing system as just described, so that a material can be characterized. In one embodiment, it is an object to provide means for importing pre-existing material test data into the information processing system for characterization to obviate at least some measurement trials.

In another embodiment, it is an object to provide mechanical testing means that imposes varying influences such as stresses and temperature conditions upon one or more material samples over time, those conditions probing the range of properties associated with the model parameters, such that the information processing system can reliably and accurately resolve those parameters from the test data. It is a related object to simplify the mechanical testing means, and to minimize the number of samples of a given material required for a characterization, and to abbreviate the time period required for characterization, in order to optimize the overall economy and utility of the mechanical testing means and associated information system, consistent with the overall system yielding accurate characterizations of materials over a usefully broad range of dynamic conditions.

It is a further related object that the testing means measure stress/strain responses for both increasing and decreasing or reversing stress, that both the increases and decreases include rapid increases and rapid decreases, that the measured responses further include response to stresses sustained for long periods and responses for sustained recovery periods after stress reduction or removal or reversal, and that these varied response measurements include responses from widely differing temperatures.

In a related context rooted in the same phenomena of thermal physics and the same fundamental statistical analysis approach, it is an object to characterize ferromagnetic and ferrimagnetic materials, both permanent and "soft" materials, through an improved model, through a method for matching model parameters to empirical data, and through devices and methods for improved testing, to probe deeply into the response space of the material.

LIST OF FIGURES

FIG. 1 illustrates allowed quantum energy levels and the associated Schrödinger wave function shapes for a one-dimensional binary strain transition domain, characterizing a localized molecular strain rearrangement in a mechanical solid., FIG. 2 illustrates energy levels as in FIG. 1, without the wave function shapes, along with a representation of the high and low points and motions of an oscillating virtual particle, being a classical representation of a quantum state confined to the lower energy potential well of the binary domain.

SUMMARY OF THE INVENTION

Figure 1:
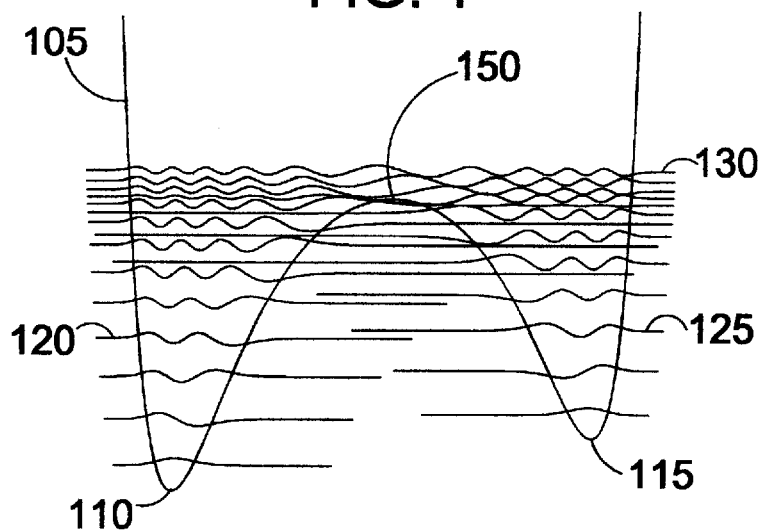

The invention is divided conceptually into three components:
1) a dynamic, non-linear, temperature-dependent statistical model of stress and strain;
2) a data processing method incorporating the model and test data and determining values for parameters of the model that minimize an error function of differences between simulated and measured data, to derive a mathematical model which best represents the test material; and,
3) means for obtaining the needed test data.

The third component is subdivided into two categories: a system that relies on preexisting or separately generated empirical data, providing means to import those data values; or a mechanical testing system to obtain appropriate data from new samples. Each of these components will be described separately and in this order, that the reader may develop the background underlying the invention.

Component I—Statistical Mathematical Model:

The first component is a novel modeling system combining elements of empiricism and theory, and rooted in statistical mechanics. The parameters of the model; however, are determined entirely from macroscopic stress/strain testing, without reference to the chemistry or physical processing of the sample to be characterized. To understand the novelty and utility of the present invention as a whole, it first is necessary to understand this model and how it is derived.

The model predicts nonlinear dynamic behaviors spanning a wide range of stress, temperature and time duration. The software is not unduly complex, though the computations require significantly more time and resources than a linear dynamic model. The model describes and utilizes one or more of three types of material energy domains. Each of these types describes a virtual particle moving along a one-dimensional path. The motion of the "particle" represents a localized, microscopic mechanical strain, and a graph defines potential energy as a function of that strain. Large numbers of such domain particles, having differing associated energy graphs and differing geometric interactions with prevailing stress and strain, collectively define a dynamic statistical model. In the context of this patent, a dynamic model shall be defined as a model that explicitly incorporates time delay, as quantified by differential equations in time. A statistical model shall imply a model having properties associated with the science of statistical mechanics, specifically a model involving the statistics of large populations of microscopic elements, whose individual properties vary and are arrayed over various dimensions, such as the dimension of energy barrier height, intrinsic energy differential, energy coupling with outside influences, and other properties to be defined below. Those elements and their statistics define the measurable macroscopic behaviors of the model, such as stress and strain. A nonlinear model is defined by traditional mathematical definitions of nonlinearity, particularly that a proportional change in the magnitude of an input variable results in a non-proportional change in the affected output variable. The collection of models described herein are characterized as dynamic, statistical, nonlinear, and also temperature dependent, as will be seen. The models are applicable to polymeric solids, including rigid plastics and rubbers, as well as to the creep characteristics of metals. The models apply to semisolids and liquids. They apply, in an altered geometric context, to ferromagnetic materials, where stress and strain are defined in terms of H fields and B fields. These models differ from traditional models applicable to stress and strain in a wide variety of materials, even though models incorporating some of these characteristics have been used for analyzing narrow classes of materials.

The simplest type of domain is a single potential well, typically parabolic in shape, confining the virtual particle and restoring the particle toward a minimum potential. This simple domain model describes a simple linear elasticity and is a meaningful representation of reversible elastic stress and strain in a crystalline solid like spring steel. The minimum potential location is a reference zero strain at zero stress. External stress from the material surrounding the domain sample in question tilts the potential graph, moving the location of the minimum potential to the left or right and redefining the equilibrium strain. The coupling of external stress to the slope imposed on the potential energy graph defines a characteristic microscopic area associated with the stress/strain interaction at the molecular level.

It is found that in a material, the stress tensor operating on the vector representation of this area produces a localized force, which in turn defines the imposed energy slope. Thermal agitation excites the virtual particle, causing an oscillatory vibration in a classical domain model, or elevation to an energy state above the ground state. The average thermal excitation energy for the domain is the product "kT" where "k" is Boltzmann's constant and "T" is absolute temperature. The probability of a given elevated energy state as a function of state energy "E" varies in proportion to the Boltzmann Factor, which is a relative probability "p" given by Eq. 1:

$$p = EXP(-E/kT) \quad 1]$$

Boltzmann Factor, a relative probability

The sum of probabilities "p" over the available energy states of the system must be unity, which yields an absolute or normalized probability, $p_n$, of finding the system in a given energy state:

$$p_n = p / \Sigma p_i \quad 2]$$

normalized probability of a given energy state

The denominator on the right side of Eq. 2 represents the summation over the relative probabilities of all the energy states, of index "i", accessible to the system, while the numerator is the relative probability of the particular state in question, given by the Boltzmann Factor.

Appropriate normalization to a unity sum of probabilities yields the absolute probability that a domain will be found at a given energy excitation level at any hypothetical instant of observation. Finally, the natural frequency of the particle in the potential well, characterized by angular frequency $\omega_o$, combined with a related resonant quality factor, Q, associated with coupling of energy between the specified domain and the thermal environment, defines a frequency bandwidth, BW, further defining how many times per second the domain energy changes from one value to a statistically independent new value, due to thermal coupling between the localized domain and its thermal environment. This bandwidth, BW, takes the form of Eq. 3, where the coefficient K is a number, on the order-of-magnitude of one, relating resonant frequency and quality factor to the number of statistically independent new energy levels per second:

$$BW = K \cdot \omega_o / Q \quad 3]$$

frequency bandwidth

Combining this "thermal coupling frequency" with the energy probability distribution defines the "time-probability" called $p_t$, a probability per-unit-time, that the domain energy will achieve a specified energy state at energy E during a unit time interval (normally one second):

$$p_t = BW \cdot p_n \quad 4]$$

probability/time of energy state

Equations 1 through 4 are unimportant to the stress/strain analysis of the single-well domain being described, but they become useful for more complicated domains, as will be shown.

A meaningful analogue to a one-dimensional single-well potential model is an electrical circuit consisting of an inductance L, a capacitance C, and a resistance R, which can be a series or parallel resistance in alternative "LCR" models, or a combination of both. A given LCR circuit will have, associated with its resonance, a natural angular frequency $\omega_o$ associated with the product LC, and a resonant quality factor Q associated with L and C and with the one or more resistors that damp the resonance. It can be shown that for a series-connected LCR circuit, the average energy stored in the "LC" inductor and capacitor combination equals kT, because the current traveling through the LC combination is confined to one dimension, defining a single degree of freedom according to statistical mechanics.

This average energy, and its temporal fluctuations, are associated with thermal or Johnson noise from the resistor R, shaped by the resonance and bandwidth of the overall LCR circuit. The bandwidth associated with fluctuations in thermal energy over time is given by BW in Eq. 2. This LCR system may be modeled as a one-dimensional virtual particle in a potential well, whose available energy levels are defined by Schrödinger's equation. The time-probability for this LCR reaching a specified energy excitation level is given by Eq. 3. This well-understood electrical system may be compared formally to the one-dimensional strain domain described above. The reasoning outlined here is then extended to more complicated and interesting domains, as explained below.

Figure 2:
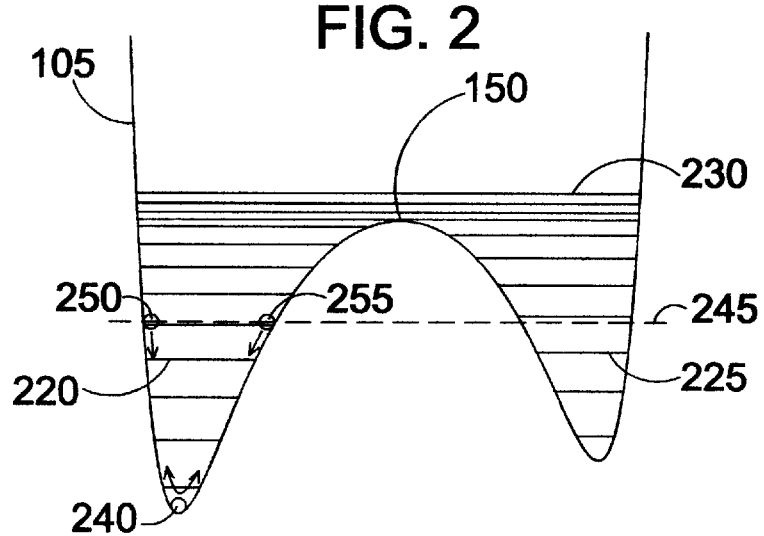

Thermal agitation properties of the single-well domain are not particularly useful in a solid state stress/strain model. The properties just described do become relevant for the two-well domain illustrated in FIGS. 1, 2, and 3. FIG. 1 illustrates the energy states available to a typical "binary strain transition domain," in which a local molecular arrangement can be in either one of two relatively stable states, confined to one of two potential wells having minimum potentials at 110 and 115, with a transition energy barrier, having a maximum potential at 150, separating the two wells. The flat portion of the line for each graph across the two-well potential function defines an allowed energy level, while the wavy portion of the line represents the shape of the associated standing wave solution to Schrödinger's equation. FIG. 2 illustrates a classical approximation to FIG. 1, in which a particle mass oscillates, confined in one of the two potential wells, in this case at the lower potential. In FIG. 1, the flat portion of line 120 represents an allowed energy state for a virtual particle confined above potential minimum 110, with the square of the amplitude of the waveform, relative to the flat baseline, representing the quantum probability of finding the particle at a given location. In FIG. 2, the same allowed energy level is represented by flat line 220, while a classical illustration illustrates a virtual particle oscillating back and forth from a minimum potential position 240, at potential 110, to maximum-potential extremes at 250 on the outside slope and at 255 on the inside of the potential well. The total classical energy of the virtual particle is represented by the height of dashed line 245, which is seen to lie below the barrier height of 150. If the virtual particle attains sufficient energy, corresponding to one of the quantized energy levels of FIG. 1 above the potential barrier (for example, wave function graph 130 or the corresponding flat energy level 230 of FIG. 2), then the particle enters a transition energy state allowing it to pass back and forth between wells.

Classically, one would say that the virtual particle is oscillating with sufficient energy to pass back and forth over the central energy barrier. From a quantum wave function standpoint, the Schrödinger amplitudes for energy levels above the barrier potential 150, for example on trace 130, are seen to have significant amplitudes on both sides of the barrier, indicating significant probabilities of "finding" the particle on either side of the barrier if an observation is taken. By contrast, the wave functions below the barrier energy level (for example, 120 and 125, at energy levels 220 and 225 in the left and right hand potential wells) have nearly zero amplitude on one or the other side of the barrier, indicating in quantum terms that the particle is confined, with a finite but extremely low probability that the particle might "tunnel" and be found on the "forbidden" side of the potential barrier.

Figure 3:
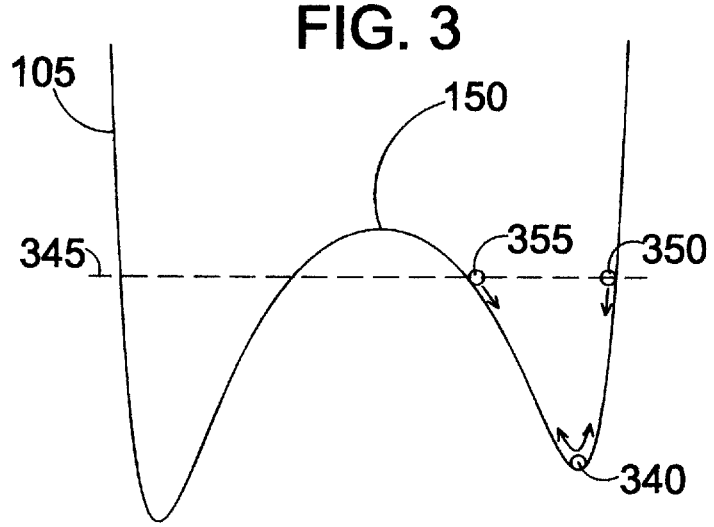
FIG. 3 illustrates the virtual particle of FIG. 2 only at a higher energy level and confined to the higher energy potential well of the same binary domain.

When the particle has had enough energy to boost it above the barrier energy level and subsequently loses sufficient energy through a quantum energy exchange, it becomes trapped in one of the wells, either the well where it started or the opposite well, as illustrated in FIG. 2 for the particle confined in the lower-energy well and in FIG. 3 for the particle confined in the higher-energy well. Thus, the particle energy in FIG. 3 is at the level of dashed line 345, below barrier height 150, and the particle oscillates between extreme positions 350 and 355, crossing minimum potential energy position 340 in either direction. In the pertinent model, the probability of finding the particle in a transition energy state, above the barrier threshold, is much less than 1.0, so that the sum of probabilities for finding the particle captured in one of the two wells is negligibly less than 1.0. The relative probability of finding the particle in the left versus the right well is defined by the sums of the Boltzmann Factors, summed over the allowable energies for each well.

The time-probability of the particle escaping confinement in one of the two wells and moving to the other is determined by the probability, per independent observation, of energy elevation to a transition energy level $p_n$ (Eq. 2), multiplied by a bandwidth BW (Eq. 3) associated with the rate of energy exchanges between the domain and its environment, yielding a time-probability equation of the form of Eq. 4. Strictly speaking, the result of concern here is the achievement of any one of the transition energy states available to the system, though the equation for an average taken over probability states approximates the result expressed by Eq. 4.

The model just described is simplified, by approximations, to be characterized by just three energy levels: an energy level E1 averaged over the statistical occupancy of energy states confined in potential well number 1 (for example, the well on the left in the illustrations); a barrier energy level averaged over occupancy of energy states above the barrier threshold; and an energy level E2 averaged over occupancy of energy states in well number 2 (for example, on the right in the illustrations.) Since no energy levels other than these three averaged levels are available to the system, the absolute energy is of no consequence. All that matters are the differences between energy levels. Thus, the three energy levels are reduced to two relative energy differentials:

$$E_d = (E1-E2)/(E1+E2) \quad 5]$$

differential energy $$E_b = \text{MAX}(E) - (E1+E2)/2 \quad 6]$$

barrier energy

In Eq. 6, "MAX(E)" represents the maximum value achieved by the energy graph between the local minima E1 and E2, while the barrier energy $E_b$ is the difference between this maximum and the average of the two minima.

We may define a "binary strain transition domain" as a grouping of particles that is altered by interaction with an external stress field, such that a slope is imposed on the energy level, altering the energy differential between the two potential wells. A state transition from one well to the other represents a strain energy release if the transition is "downhill" relative to the imposed external stress, or a thermal energy capture if random thermal agitation bumps a domain into a higher energy state. An increase in temperature increases the probability that the domain particle will be found in the well of higher energy. An increase in temperature also reduces the average time between state transitions, thus softening the material from a macroscopic viewpoint.

Each strain transition, from one potential well to the neighboring well at a different potential, has an associated physical volume, such that the product of volume times stress magnitude equals the change in strain energy. The volume can be imagined as the volume swept out by the displacement of atoms or molecules during the strain transition. This approximate definition will be refined by discussion below.

Examining the detailed coupling of a domain to the external environment, any strain transition represents a localized rearrangement of molecules in a solid. Such a rearrangement is illustrated schematically in FIG. 4, where on the left, two polymer chains lie against each other with complete overlap of four monomer units of length along the coupled chains 405 and 410, and partial overlap for some additional length. The forces linking the chains are molecular bond forces, also known as Van der Waals forces, being relatively weak bonding forces in bonds many of which are disrupted by thermal energy when a material melts. The energy per molecular bond in the material is of the same order of magnitude as the molecular heat of fusion divided by the number of molecular bonds that are disrupted by the melting process. These molecular bonds are generally much weaker than ionic or covalent chemical bonds joining units of a polymer strand.

Thus, in the binary strain transition domain model, melting is viewed as a thermal process sufficiently energetic to facilitate frequent strain transitions in molecular rearrangements without destroying the polymer chains that are being rearranged. In the strain transition illustrated, a shear stress promotes a shift in the overlap of the two strands. Where each of several polymer units was in close proximity to two units of a neighboring strand at equilibrium, these units have only one close neighbor during a strain transition, as in the middle of the three drawings, causing an elevated energy state. At the end of the transition, most of the polymer units are again close to two neighbors instead of one, although the number of neighbor pairings may be altered, so that the potential at the end of the transition may not equal the energy at the beginning, even in the absence of external stress.

Figure 4:
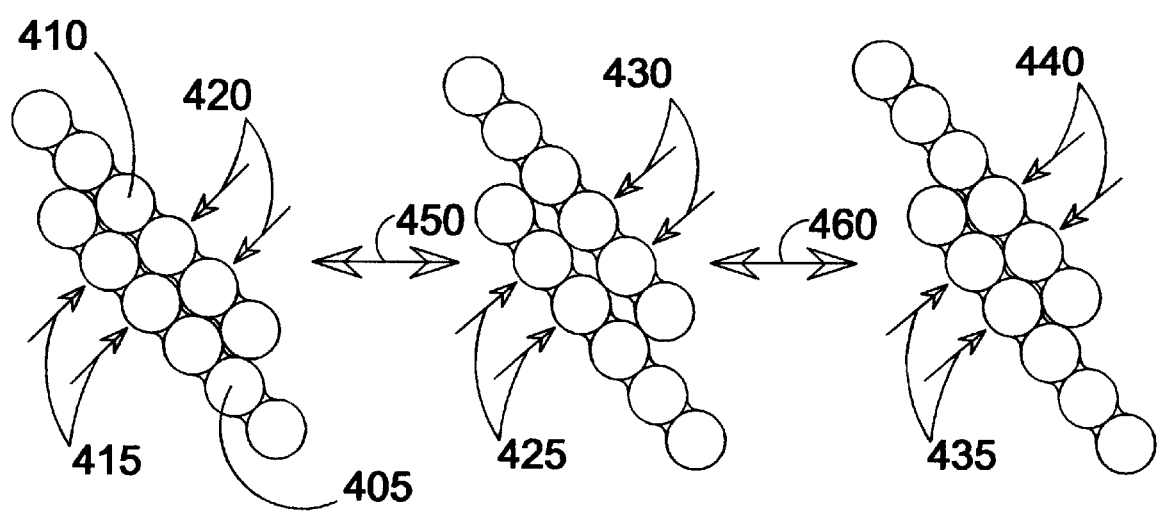
FIG. 4 illustrates three stages of a hypothetical strain transition between two linear polymer molecules, from equilibrium with complete overlap of four polymer units, to a higher energy state in transition with less contact between neighboring molecules, to a new equilibrium at a slightly higher energy than the original equilibrium and with complete overlap of only three polymer units.

In the right hand drawing of FIG. 4, a lesser complete overlap of three rather than four molecular units is illustrated. Reference arrows 420 on chain 410, and arrows 415 on chain 405, illustrate positions in a lower potential well before a strain transition. Double arrow 450 represents transition between minimum energy and maximum energy at the top of the potential barrier, where reference arrows 415 and 420 have moved to positions 425 and 430, with the molecular chain units located directly opposite one another with minimum molecular overlap. Double arrow 460 represents the transition from maximum energy down to the local energy minimum of a right-hand potential well (as in FIGS. 1, 2, and 3). Reference arrows 425 and 430 have moved to positions 435 and 440 in the right-hand illustration, no longer directly opposite but offset to give a local maximum in the overlapping contact between molecular chain units. Thus, we say that a strain transition domain may have an intrinsic potential difference at zero external stress, as well as a stress-induced change in potential difference from the baseline intrinsic value, depending on the degree of overlap of polymer chains, and depending more generally on strains that bend and pull at the chains. It is understood that the statistical mechanics described here applies to all possible local arrangements and rearrangements of molecules in a solid. One need not know about the specific geometries of these arrangements to obtain useful results from the model. One need only determine, from empirical macroscopic properties, the statistical properties of molecular arrangements of the sort illustrated, including complex three-dimensional variations.

To emphasize, the practical use of this empirical statistical approach is to characterize what is macroscopically important about molecular rearrangements in a complex solid material, without requiring specific knowledge of what those arrangements and rearrangements look like. In a solid with n particles, there are roughly 3n degrees of freedom, defining a state space of very high dimensionality. Within that state space, we can focus our attention on one localized area where there are two possible arrangements that are relatively stable and with a transition path from the one to the other. For each arrangement, there is a configuration that represents "rest" or the bottom of the potential well (in quantum mechanics, the "ground energy state"). The line connecting these two minimum potential configurations defines a one-dimensional path through the 3n-space. We say that of all the thermal vibrations of the solid, the alignment of vibrations that promotes this specific state transition in our domain is just one direction, along this one-dimensional path. We view this transition as being excited by one-dimensional black body radiation, equivalent to the noise power in an LCR circuit contributed by the resistor, while our system of concern, the binary domain, carries an average thermal energy kT, with temporal energy variations associated with the power level of black body radiation over the bandwidth in which the domain is readily excited.

Before considering further details of the geometries of microscopic strain transitions, we are in a position to look at the statistical dynamics of a large collection of identical binary strain transition domains, representing an average response over similar regions dispersed through the volume of a solid. The input to the model is an externally imposed stress, P, whose influence is experienced locally as a domain energy differential $E_d$, as defined in Eq. 5. The domain energy barrier is $E_b$, as in Eq. 6. The strain state, S, of the statistical collection of domains is represented by a scalar number equal to +1 if all the strain states are positively aligned with respect to the imposed stress P, and −1 if all the strain states are oppositely aligned. The time-independent equilibrium value for S, called $S_e$, is given by Eq. 7. For given values of the differential energy $E_d$, barrier energy $E_b$, effective bandwidth BW for energy state changes, and absolute temperature T, Eq. 8 gives the settling rate, RATE, for exponential decay of S toward the equilibrium value $S_e$. This RATE is the reciprocal of the exponential settling time, τ. A rate is chosen, rather than the familiar reciprocal, as being useful to illustrate "fast" versus "slow" settling, such that "larger value" means "faster".

$$S_e = \tan h(E_d/kT) \quad 7]$$

equilibrium strain $$RATE = BW \cdot exp(-E_b/kT) \cdot \cos h(E_d/kT) \quad 8]$$

strain equilibration rate

It is understood that BW, as defined in Eq. 3, will include some correction factors built into the scaling coefficient K, for example, to account for the probability that when a domain is boosted into a transition energy state, it falls back into the opposite state with a state transition, rather than falling back into the same state. A typical bandwidth BW may be on the order of $10^{12}$ per second or somewhat higher (for example, $10^{13}$). Compared to a settling RATE=1-per-second, meaning an exponential settling time of 1 second, an order-of-magnitude error in BW is compensated by a change of less than 10% in $E_b$ (for example, one part in 12 or 13 for the proposed typical bandwidths), because $E_b$ is in the argument of an exponential function. For empirical modeling, therefore, BW need not be known accurately, but only very approximately, so that the energy barrier magnitudes are about right in relation to the thermal energy magnitude kT, causing the model to give the correct temperature dependence. One of the merits of this model is that, when properly based on constraints of the underlying physics, temperature dependence comes out correctly, without extra parameters set arbitrarily.

Figure 5:
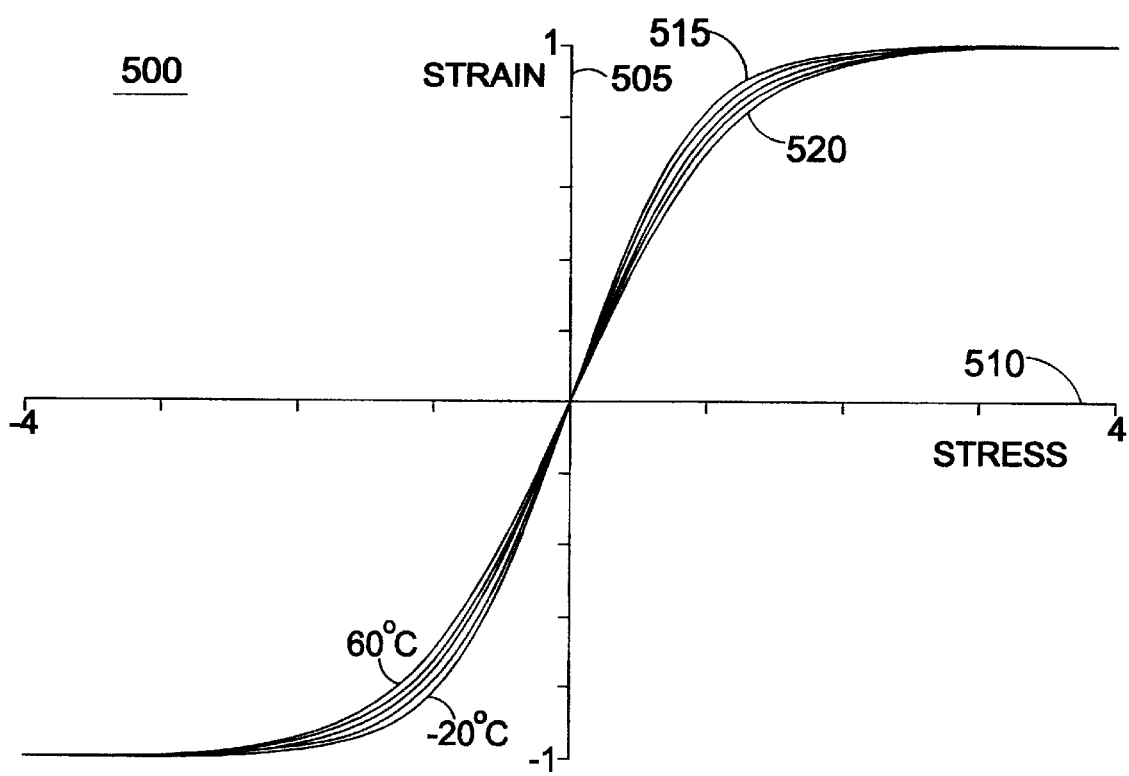
FIG. 5 illustrates a family of curves, arrayed over temperatures, for equilibrium strain as a function of stress, the strain response being averaged over many domains having identical physical characteristics and responding individually to the same stress but with random thermal agitation.

Behavior of Eq. 7 is illustrated in FIG. 5 by graph 500, for temperatures varying on either side of 20C, from −20C to +40C, going from curve 515 to curve 520. One unit along horizontal axis 510 is scaled to the energy kT for T=293K, that is roughly 20C, the reference temperature.

The vertical scale 505 varies from −1 to +1, as defined for the normalized strain function. Observe that the temperature dependence is weak, with the steepest curve corresponding to the lowest temperature, indicating the largest rate of change of equilibrium strain for a given change of stress near zero. At a constant stress level on the horizontal axis, therefore, the equilibrium strain is highest at the lowest temperature and decreases with increasing temperature. One can say that thermal agitation tends to randomize strain states, driving $S_e$ toward zero from a more systematically aligned state of high strain. Heat increases entropy, randomizing the alignment of states.

Figure 6:
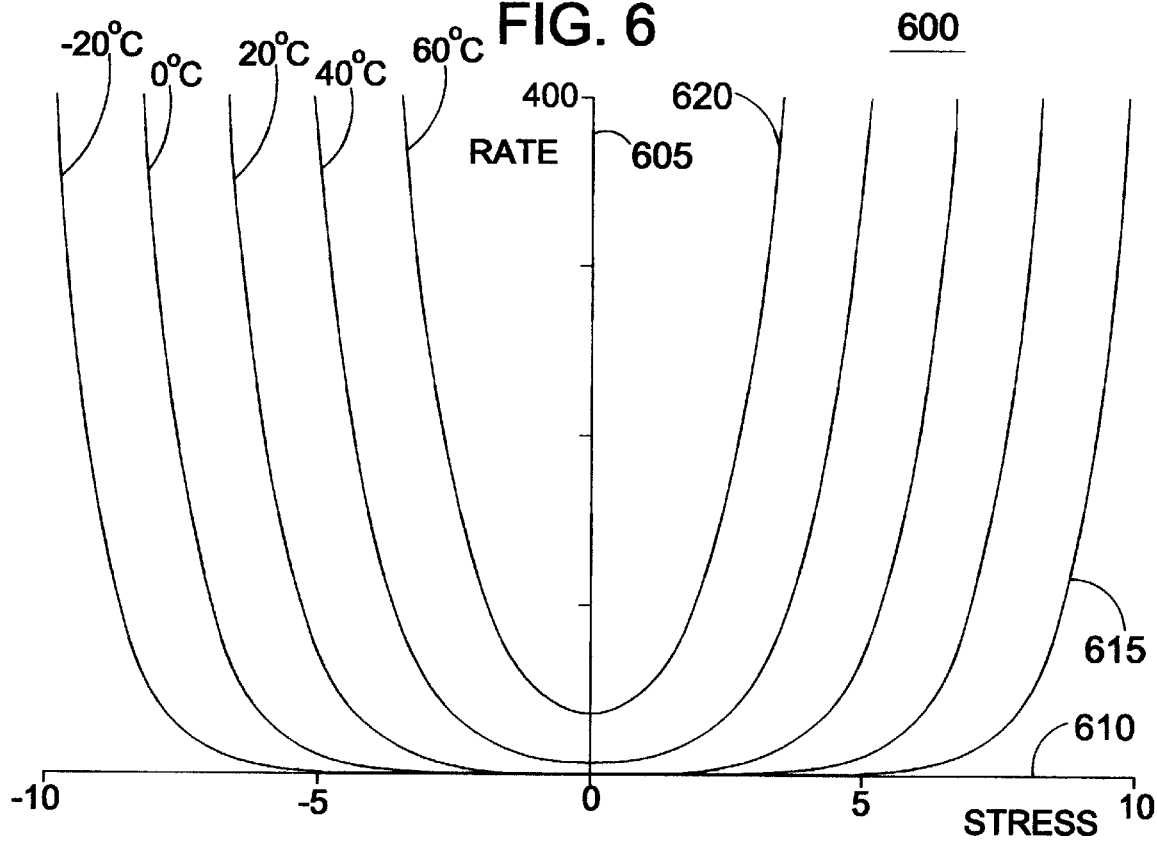
FIG. 6 illustrates a family of curves, arrayed over the same temperatures as in FIG. 5, for exponential rate of settling toward the equilibrium value of FIG. 5. The rate is a function of the same normalized stress indicated on the horizontal axis of FIG. 5, except that FIG. 6 illustrates a wider stress variation on the horizontal scale.

Behavior of Eq. 8 is illustrated in FIG. 6 by graph 600. The horizontal axis unit along 610 is the same, although the horizontal scale in FIG. 6 spans a larger range (from −10 to +10) than in FIG. 5 (from −4 to +4) to illustrate the significant behaviors of the RATE function, for curves arrayed over the same temperatures as in FIG. 5. The rate function is scaled vertically, along axis 605, such that at 20C and zero stress, RATE=1. Curves 615 and 620 show the rate function at temperatures of −20C and +60C.

The temperature dependence of the equations is based on BW=$10^{13}$, implying that for RATE=1, the virtual domain particle gets over the potential barrier and is captured on the opposite side of a symmetric potential well with a probability of one in $10^{13}$ per "try", where an independent "try" is defined as a new thermal energy measurement taken just long enough after a previously measured energy level to bear little statistical correlation with the previous energy level. The vertical scale as illustrated goes to 400; that is, RATEs are plotted up to 400 times faster than the baseline RATE at room temperature and zero stress. At the highest temperature, strain equilibration is comparatively fast even in the vicinity of zero stress.

One might characterize the warm material as "soft" and able to stress-relieve internal strains fairly quickly by plastic flow. The warm material is not strong, relatively speaking, in that it yields easily at low stresses. At the lowest temperature, strain equilibration is much slower at low stress levels (unreadable on the graph, minimum RATE=0.0088 per second, as compared to the reference at RATE=1.0), so that the material would be characterized as hard or frozen on a time scale of one second. (Hardness or brittleness is a time-dependent characteristic. The cold material described here would start to appear plastic rather than brittle on a time scale of 100 seconds.) At a sufficiently high stress level, the strain equilibration rate reaches a discernable magnitude on the graph as a sharp exponential elbow. Although the hyperbolic cosine RATE function has no definable elbow between comparatively flat and curving regions, one can characterize the response by an elbow that distinguishes between strain rates much slower than, and much faster than, a given rate of strain application.

If strain is imposed at a value corresponding, for example, to a RATE value that is 100 times larger than the zero-stress RATE, meaning roughly 100 times as fast as the reference material can undergo plastic flow in a linear range of behavior, then unrelieved stress will build up rapidly, at a rate determined by the short-term elastic modulus of the material, until the buildup is limited by a hundred-fold increase in RATE. Such a highly nonlinear characteristic will be associated with brittle behavior, since nonlinear failure mechanisms will predominate. When stress reaches the rapid yield threshold in a localized region, rapid strain in that region releases the stress that was supported in that region, transferring the stress to the edge of the region, where additional material yields.

The material will sustain some stress elastically, due to linear elastic behavior modeled by single-well energy domains and/or by linear perturbations in strain with stress as domain virtual particles shift back and forth within the confines of single potential wells within binary domains. As the material yields locally in rapid strain, elastic rebound of surrounding material will momentarily keep the region of rapid strain going at an accelerating strain rate as stress is transferred to the edge, widening the region of rapid strain. The result, going beyond the valid confines of the model being presented here, is to attain a new sort of failure mode, for example, where molecular strands separate or where chemical bonds of the polymer molecules are broken.

Thus, the nonlinear character of the model embodies characteristics associated with low-temperature cracking and with tear propagation in sheets, where the same material can better resist cracking, and can stretch without tear-propagation, at higher temperatures. In many practical applications, the domain model need not include sufficient detail to model the final stages of failure at rupture, provided that the model identifies the runaway behavior that unmistakably leads to failure.

Observe, finally, that the very nonlinear behavior of the low temperature graphs of FIG. 6 occurs at stress magnitudes where the transition energy exceeds double or triple the energy magnitude kT, that is where the equilibrium strain approaches "saturation," meaning a low-entropy state of maximum alignment of molecular arrangements with no latitude for further alignment. This is a meaningful comparison, not just an artifact of arbitrary choices for the scaling of these functions. For a given type of domain within the array of types in a material, the result implies that if stress is ramped up past the threshold where RATE catches up to the speed at which stress is being applied, then the domain population will jump abruptly to a state of saturation. For a given type of domain, the model implies approximately linear tracking of strain lagging behind stress only at stresses insufficient to cause saturation. Conversely, highly nonlinear equilibration occurs only at stresses sufficient to cause saturation at equilibrium.

Nonlinear, temperature-sensitive, time-dependent, dissipative stress and strain in solids, especially polymer solids and elastomers, is characterized by a time-independent equilibrium behavior with weak temperature dependence and strong nonlinear saturation, coupled with a time-dependent behavior that is strongly temperature dependent and can exhibit a sharp nonlinear rate threshold for stress. Behavior of a complex solid sample will be characterized by statistical averaging over types of domains having different energy barriers $E_b$, different couplings between domain energy differential $E_d$ and an external stress, and different intrinsic energy differentials of $E_d$ at zero external stress. This averaging will mask the strong nonlinear characteristics just illustrated for a group of domains having nearly the same energy barrier, nearly the same coupling to external stress, and nearly the same intrinsic energy differential.

A strain transition represents a localized rearrangement of molecules, going from one relatively stable configuration to another, as influenced by thermal agitation and external stress. A strain transition causes a perturbation in the shape of the surrounding material, such that an imaginary spherical shape would be perturbed into a non-sphere. At a sufficient radius from the center of a strain transition, the deformation of a reference sphere yields an ellipsoid, with higher-order shape perturbations becoming comparatively much smaller than the ellipsoidal perturbations at large radii. This strain ellipsoid defines a strain tensor, characterized by a strain magnitude, an ellipsoidal shape, and an orientation of the three principal axes of the strain ellipsoid in space. This strain tensor represents a shear strain at constant volume, since volume perturbations have little influence to rearrange molecules, tending only to squeeze them more or less tightly together.

Figure 7:
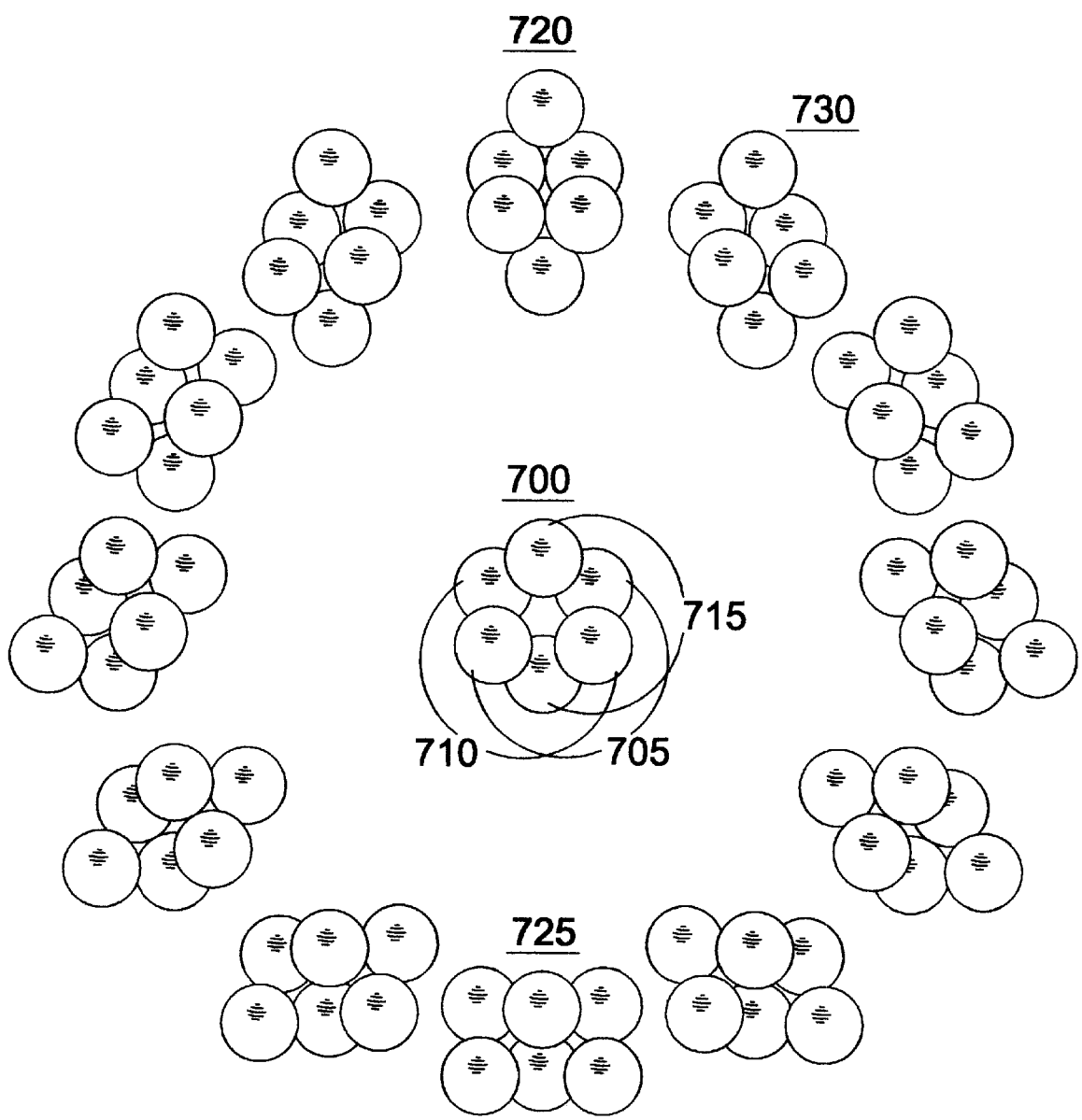
FIG. 7 illustrates strain shapes associated with strain ellipsoids at constant perturbation amplitude from a reference sphere, as those shapes vary continuously in a mapping of those shapes to angles in a circular array of shapes. This shows how shape variation in shear strain can be represented by a single angle parameter having a period of $2\pi$ radians.

The possible shapes associated with shear strain at constant strain energy and for fixed principal axes of strain are illustrated by the circular array of shapes of FIG. 7. The central collection 700 of three pairs of spheres, spaced equally along three principal axes for pairs 705, 710, and 715, indicates a reference shape at zero strain corresponding to a reference sphere, before it is distorted into an ellipse. The twelve circularly arrayed shapes, separated by 30 degree angles along a circle, represent points along a circularly-mapped continuum of shapes, giving maximum elongations and maximum compressions along each of the three principal axes.

Specifically, maximum elongation along a first principal axis, appearing along the vertical in the isometric projections of the diagram, is represented by the shape 720 directly above the unstrained symmetric center shape, at an angle of 0° with respect to the vertical direction of the array diagram, while maximum compression along that vertical principal axis is represented by the shape 725 directly below the unstrained center shape, at an angle of 180° in the array diagram. The elongation and compression along this first principal axis varies as the cosine function of the angle away from vertical in the array diagram. Similarly, elongation and compression along a second principal axis varies as the cosine of the diagram angle with the addition of a phase offset of 120°. Elongation and compression along a third principal axis has a phase offset of 240°. Observe that while shapes 720 and 725 represent extremes of extension and compression along a single principal axis, with symmetric expansion and contraction along the remaining two axes, shape 730 and its 180-degree opposite are qualitatively different. In these two shape perturbations, the particle spacing 710 of the central cluster remains unchanged, while the remaining two axes undergo contractions and expansions of equal magnitude. Thus, in the continuum of shapes encountered going between the illustrations of FIG. 7, one encounters two essential strain symmetries.

The sum of the squares of the length perturbations over the three principal axes is a constant sum, representing a constant strain energy throughout the range of angles. This mapping as a function of diagram angle captures all the possible shape perturbations for shear strain along fixed principal axes, while the amplitude or small-perturbation energy associated with each shape may be mapped to varying radius in a two-dimensional representation of all possible shear stresses or strains confined to fixed principal axes. This mapping of the shape degree of freedom is used, in conjunction with energy correlations over varying spatial orientations of the principal axes, to define distribution functions for energy couplings between external stress and localized strains, as explained below.

The local strain tensor may be represented as a 3×3 matrix, or Cartesian tensor, the tensor being symmetric and having a zero trace, that is having a zero sum of the three elements on the main diagonal. Like the strain tensor, a stress tensor is characterized by a similar matrix. A specific kind of matrix product, which shall here be called the tensor dot product, defines the interaction energy between a local strain tensor and an external stress tensor. This energy is the domain transition energy between potential wells, as described above. This energy is defined by the product of three terms: a magnitude of the stress tensor; a magnitude of the local strain tensor; and a factor called "COS" that varies between −1 and +1. This tensor COS factor is analogous to the cosine of the angle between two vectors when a vector dot product is taken.

The value of COS depends on the relative shapes of the ellipsoids associated with the strain and with the stress. The "shape" of a stress tensor is defined by the ellipsoidal shape resulting when a reference sphere in a linear, isotropic, homogeneous elastic solid is perturbed from spherical by the stress. When the amplitude-normalized shapes of stress and strain are congruent, then we define the shape correlation factor as 1.0, or otherwise the shape correlation factor is less than 1.0, and possibly negative. The value of COS also depends on the relative orientations of the principal axes of the stress and strain tensors. The orientation difference and the shape difference together define the value of COS. When shapes are congruent and the orientations are congruent, then COS=1.

For an ideal isotropic material, strain domain orientations are random. It is believed that the shapes of the strain transition ellipsoids are also randomly distributed among the possibilities mapped to $2\pi$ radians of circular angle in FIG. 7. The hypothesis used here is that no angle in the shape mapping illustration of FIG. 7 is statistically favored over any other angle. (If experiments contradict this hypothesis, then the model described here can be corrected appropriately.) With a chosen shape probability distribution in place, for example, with an equal-probability distribution over the angle mapping of FIG. 7, then one can define a probability distribution for the magnitude of the factor COS. This distribution goes to zero probability density at the extremes of COS=−1 and COS=1, is symmetric about the axis at COS=0, and resembles a bell curve with a maximum probability density at COS=0. The use of this distribution function will be discussed below.

Figure 8:
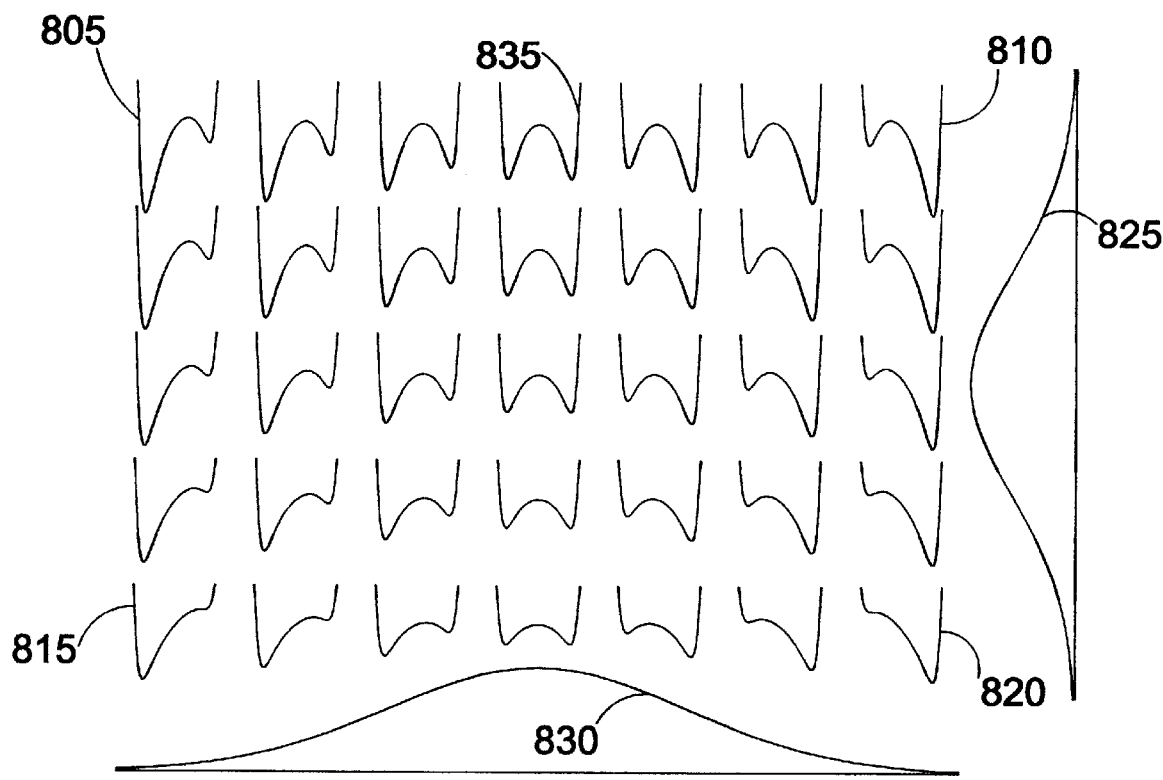
FIG. 8 illustrates an array of strain transition domains having differing potential barrier heights and differing intrinsic energy biases, along with bell-curve population density functions indicating the distribution of domain populations over barrier height and intrinsic energy bias.

FIG. 8 illustrates an array of strain transition domain types having differing potential barrier heights, arrayed vertically, and differing intrinsic energy biases, arrayed horizontally, along with bell-curve population density functions indicating the distribution of domain populations over barrier height (curve 825) and intrinsic energy bias (curve 830). For barrier height, the bell curve has a specified mean value and a specified dispersion width. For intrinsic energy bias, the center of the bell curve is at zero, while the dispersion width represents another independent distribution parameter. Along a third axis, emerging above and going below the illustration on the page, one also has the distribution associated with the probability for various values of the factor COS. For a specified plane along this third axis, specifically for a non-zero value of the factor COS, then an external stress magnitude results in a systematic biasing of all the potential well energy differentials, as illustrated by comparing FIG. 8 with FIG. 9.

Figure 9:
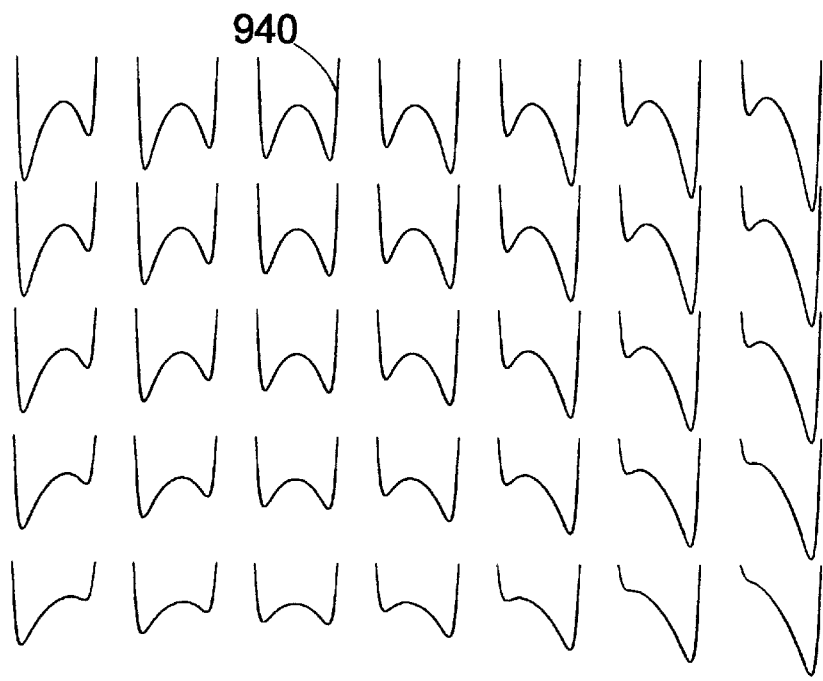
FIG. 9 illustrates the domains of FIG. 8 modified by a constant perturbation in the energy differentials between the paired potential wells, representing a particular interaction with an external stress field to modify the energy differentials.

The central column of energy graphs in FIG. 8, with symmetric wells like potential graph 835, becomes the column one over to the left of center in FIG. 9, with the symmetric graph found off-center at 940, as an external stress alters all the potential distributions. The intrinsic bias extremes of the FIG. 8 distribution are between curves 805 and 815 for a deep left-hand potential well, and curves 810 and 820 for a deep right-hand well. The barrier height extremes are for the row between curves 815 and 820 for minimum barrier, and between 805 and 810 for maximum barrier. The most probable alteration from an external stress is associated with COS=0, the center slice in the layers from COS=−1 to COS=+1. In this case, external stress does not influence the potential wells. Moving away from the center layer, there is an increasing positive or negative influence of stress on the potential energy difference.

Many isotropic materials may be characterized fairly thoroughly and accurately by six parameters, governing distribution functions like those discussed. First, there is a mean and a dispersion for energy barrier height—two parameters. Then a dispersion for intrinsic energy bias—a third parameter. Next, there is both a distribution with a mean value, and a dispersion, for the volumetric size associated with each domain, as defined above, such that the product of strain volume times stress magnitude gives strain transition energy, yielding the fourth and fifth parameters. This volume parameter can be visualized roughly as the volume swept out by the motions of molecules rearranging themselves in a strain transition, to the extent that the swept volume correlates with the shape of a perturbation from a sphere to a strain ellipsoid. The magnitude of a strain volume characterizes the maximum degree of coupling whereby an external stress alters the energy differential between paired potential wells. This coupling is reduced by the distribution of the COS factor, but for isotropic materials, the COS distribution does not add another variable parameter; for the isotropic case, the COS distribution is considered to be fixed and universal.

Finally, added to the means and dispersions of these normalized distribution functions just described, one has a scaling magnitude for the whole, the sixth independent parameter of the "standard polymer model." The statistical distributions over domains provide absolute scales for the energy barriers and for the strain displacement volumes, but they do not provide absolute numbers, that is, how many domains per unit volume. This net domain density is the sixth parameter, a total number of domains per unit volume.

The following list summarizes these six parameters for the isotropic "standard polymer model."
Standard Polymer Model Parameters:
1) energy barrier height, mean
2) energy barrier height, dispersion
3) intrinsic energy bias, dispersion (about a zero mean)
4) strain volume magnitude, mean
5) strain volume magnitude, dispersion
6) total domain density These six parameters, however, neglect linear compliance. Single-well domains exhibit linear compliance, and binary domains exhibit linear compliance at a level well below the threshold stress that overcomes the potential barrier and causes an abrupt state transition. The linear compliance is lost in the simplification of the domain description to just three energy levels with two energy differentials. Within a given class of materials, linear compliance is restored to the model as a single linear compliance coefficient, whose value is not very sensitive to temperature and whose value is expected to be fairly constant within a class of materials. Strictly speaking, linear compliance must be considered a seventh independent parameter of a relatively complete model.

Experience may reduce the number of parameters required to adequately characterize a polymer material. For example, the displacement volume associated with a domain depends largely on the number of polymer units involved in the transition. The energy barrier also depends largely on the number of polymer units. Within a specified class of materials, a consistent correlation between displacement volume and energy barrier may reduce the number of independent parameters needed for characterization. Similarly, the breadth of the intrinsic bias distribution may prove to vary little within a class of materials, again reducing the number of independent parameters to be determined from data for new samples. Such reductions may result in good fits from less empirical data, reducing the complexity and/or duration of testing needed to obtain a good model.

Computationally, the state of the solid is represented by a multidimensional array of strain parameters, "S," numbers varying between −1 and +1 and indicating the population distributions in domains of a specified type, according to potential barrier height, intrinsic energy bias, and effective volume coupling for a domain of this type to a specified type of external stress. Note that this is a three dimensional array, less than the dimensionality one might suspect from the count of six material parameters described above. The dimensional reduction comes about because domains having the same product of volume magnitude multiplied by the factor COS are treated in the same way. It does not matter to what extent strain is promoted by volume displacement magnitude as opposed to energy correlation arising from differences in shape and orientation.

Thus, the six parameters characterizing a material by the standard model are reduced to a more manageable three dimensions prior to dynamic simulation. The dimensions for the dynamic variables $S_{ijk}$ can, for example, be 5×5×5, yielding 125 dynamic variables to track over time. Even a 2×2×2 array, with just eight dynamic variables, can yield useful but approximate insight into the strain behavior of a material. It is believed that mathematical methods will be found for yet more efficient representation and computation of the arrayed variables $S_{ijk}$ described here. For example, there may be mathematical approximations for tracking average responses of groups of domain types arrayed along one or more axes of parameter variation, without the necessity of tracking all the separate members within each group. There will be refinements and improvements based on the model described here, preserving the basic invented structure here defined, while lowering computational cost and improving practical applications, for example, in Finite Element Analysis (FEA).

For interpreting the macroscopic strain implied at a given instant by the 3-D array $S_{ijk}$ of domain populations, populations are tallied in a weighted average according to the component of displacement volume resolved in the direction in which the material is being stressed. The COS factors described above come back into play in this process. The resulting weighted average of $S_{ijk}$ variables is then scaled according to the overall domain density of the sample. Summarizing, Dimensions of $S_{ijk}$:
1) energy barrier height
2) energy differential
3) strain displacement volume Macroscopic Strain=sum of $S_{ijk}$ weighted by strain displacement volumes and COS factors The detailed features of the dynamic integration of strain response to a stress and temperature history are readily worked out by persons appropriately skilled at numerical analysis and simulation. We note here that, given a basic time step for integration, which may be adjusted downward when things are happening quickly and upward when things are happening slowly, some domains will be virtually in equilibrium in the time frame of the time step. The states of these domains may be computed non-dynamically, simply setting the domain states to track their equilibrium values. Somewhat slower-responding domains may be represented as tracking behind equilibrium with a time lag equal to the reciprocal of the variable "RATE" defined in Eq. 8. Still slower-responding domains may be tracked based on linear exponential decay characteristics. Thus, in an iterative model for dynamic changes over a specified time step, the mean stress and rate of change of stress are estimated, after which the tracking responses of various domains are computed by an equilibrium model, or by equilibrium with time delay, or by exponential settling to a rate-dependent offset from equilibrium, or by other approximation models. The resulting time step computation may alter the overall stress estimate in the material at the end of the time interval, depending on boundary constraints, leading to revised estimates of mean stress and rate-of-change of stress, for a new iteration over the time increment.

If some domains settle in microseconds and some settle in hours or years, it is not necessary to run a dynamic simulation in time steps of microseconds over simulated periods of hours or years, if approximations like those outlined here are employed to lengthen the time steps without losing computational stability. Simulation time steps can then be varied to resolve the significant responses of a simulated material sample, using short steps immediately after a transient change in imposed stress and progressively longer time steps as responsive changes in the material slow down.

We note that the computational model is initialized, for example, to the equilibrium population biases $S_{ijk}$, which will be zero for symmetric domains and non-zero for domains with intrinsic bias. From this point, a stress is computationally applied, causing rates of change across the $S_{ijk}$ array. Within an individual domain type, that is, within a set of domains sharing a given energy barrier, a given intrinsic bias, and a given effective coupling volume to the external stress, the equilibrium value for S is $S_e$ as defined by Eq. 7, while the exponential settling rate is RATE as defined by Eq. 8. Thus, each member in the 3-D array $S_{ijk}$ of domain population types is characterized by a time-independent equilibrium function that goes to limit values +1 and −1 at positive and negative saturation, plus a time-dependent settling or equilibration characteristic, toward equilibrium, that gets faster as stress causes an increasing net differential magnitude between the two potential wells.

Because of the steepness of this rate equation, the equilibration rate at zero bias can be negligible, and the material can be effectively "frozen" into a non-equilibrium state. Heating the material promotes accelerated equilibration, even as increased temperature alters the equilibrium distributions, pushing them closer to a 50—50 population balance, or toward zero population bias as defined by S on a scale from −1 to +1. High stress greatly accelerates the settling process as it changes the equilibrium target. Thus one encounters nonlinear hysteresis in the widely varying equilibration rate equation, often exhibiting a sharp elbow from a negligible equilibration rate to a rapidly increasing rate of settling with increasing stress.

The two equations just described are applicable with differing coefficients to differing groups of domains. One of them is a time-independent equilibrium function, and the other a rate function. These equations represent the overall character of dissipative nonlinear stress-strain behavior in polymeric solids. The characteristic shapes of these functions, however, become more spread out after averaging over domains governed by different rate and saturation thresholds and with different intrinsic biases. Applying the probability distribution function for values of the coupling factor COS, even for identical but randomly oriented domains, has a strong effect of smearing the characteristic response-function shapes over a broad range of stresses and strains.

Polymer and especially elastomer materials have strongly nonlinear, time-dependent, dissipative behavior. Some metals and ceramics exhibit predominantly linear elasticity for stresses well below a defined yield point. This sort of elasticity is described by single-well potential domains, or equivalently by a linear shear modulus, in addition to a linear bulk modulus for volumetric changes with change in pressure. Bulk modulus is the scalar counterpart of tensor shear stress. At irregular boundaries between the crystals of a metal or ceramic, dissipative molecular or atomic rearrangements take place, which are characterized well by binary transition domains. Hence, for example, spring steel and beryllium copper are known to exhibit a very small stress relaxation that varies roughly linearly with the logarithm of time at constant temperature.

Logarithmic settling, the inverse of the better-known process of exponential decay, is a characteristic signature of the domain model described here, which emerges from the equations and the distribution functions just described. Thus, a complete model for metals and ceramics, including the dominant component of linear elasticity and the lesser component of dissipative temperature-dependent stress relaxation, relies on a blend of the first and second domain types, the first type readily characterized by linear coefficients.

Figure 10:
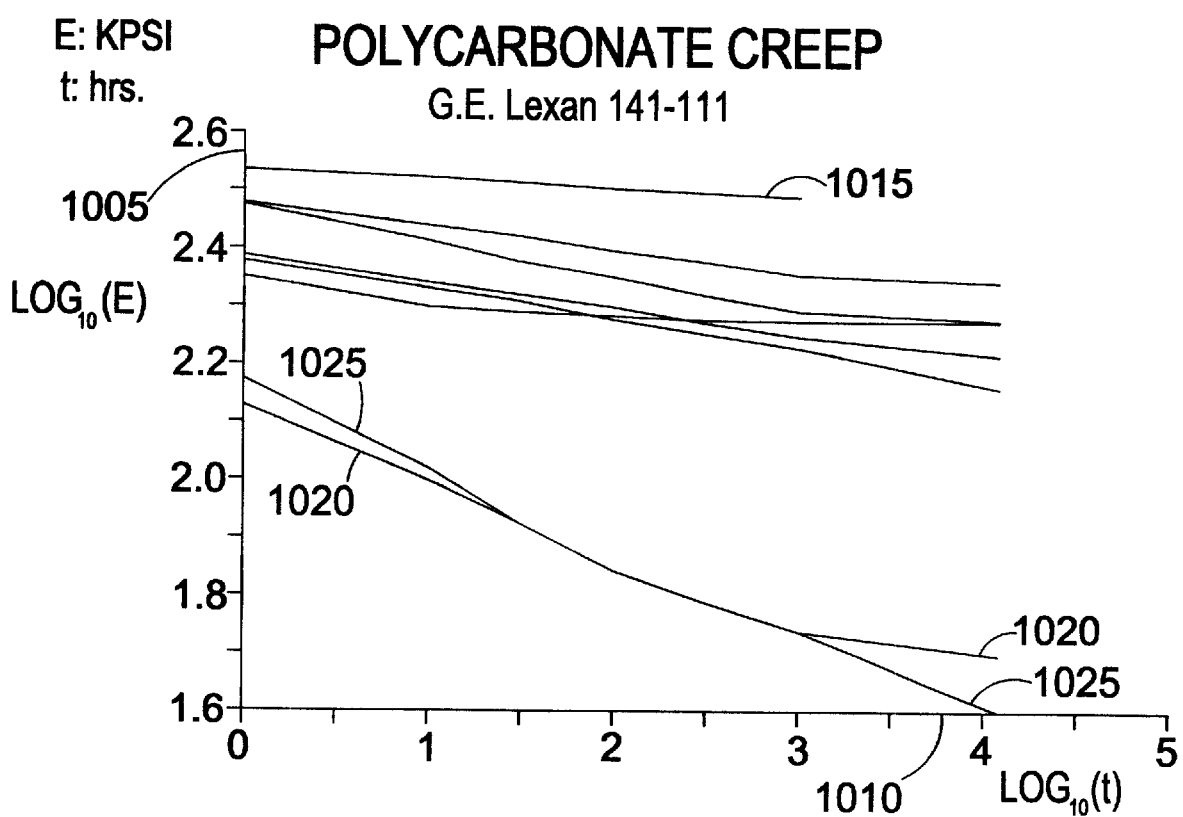
FIG. 10 illustrates existing data describing creep modulus for a common plastic (polycarbonate). The figure indicates both the temperature-dependent logarithmic stress relaxation characteristic that is readily quantified by the present system, as well as the nonlinear response to stress magnitude.

Logarithmic settling is evident in the family of curves plotted in FIG. 10, representing dynamic strain response to various fixed stress levels for samples of a common plastic, polycarbonate (source: Modern Plastics Encyclopedia, 1985–86, McGraw Hill, p. 501). While modulus is defined as the ratio of stress divided by strain, creep modulus represents that ratio as determined after the stress has been applied for a specified time interval, which is conventionally plotted logarithmically on the horizontal axis as in FIG. 10 for axis 1010. The creep modulus is also plotted on a logarithmic scale, 1005. Observe that the minimum time interval at Log(t)=0 represents one hour, while the maximum slightly beyond Log(t)=4 represents more than 10,000 hours—over a year. It would clearly be beneficial to reliably extrapolate long term creep characteristics of a material based on relatively brief tests. Plots of creep modulus versus time interval are provided for different combinations of stress and temperature.

Note that all the modulus response curves are relatively straight lines when plotted against the logarithm of time. The modulus and the slope of modulus versus log of time are lowered systematically by increasing temperature. Most of the modulus curves exhibit decreasing slope with increasing time, indicating the domain model characteristic described as saturation—an exhaustion of possible rearrangements contributing to strain in the direction of applied stress. Curves for high strain may exhibit an increasing downward slope as the material necks down in cross-section on the way to failure. The nonlinear material characteristics can cause a crossing of modulus curves for different combinations of temperature and stress, for example, where curves 1020 and 1025 cross under conditions of high temperature and high strain. Trace 1015, at low temperature, low stress, and low strain, is virtually straight. The standard polymer model described above, with its six variable parameters, plus a possible additional linear compliance coefficient, can be used in conjunction with means for data transfer and data translation, and with means for fitting of model parameters to data, to yield parameter values characterizing the material. Those values can be used in subsequent predictive simulations.

It should be noted that a sample of material might be subjected to stresses having different associated shape ellipsoids, for example, characterized by 2-dimensional sheet stretching as when a balloon is inflated (shape 725), or characterized by 1-dimensional linear stretching as when a slender sample is pulled axially (shape 720), or characterized by elongation along one axis, foreshortening along a second axis, and no effect along a third axis (shape 730). The axes of stress application might also vary during the test.

In the situation described here, both the shape and the principal axes of the applied stress are considered to remain constant throughout the test, with only the magnitude varying over time. For pure shear stress, it is believed that, starting with matching virgin samples, equivalent test results would be attained for any shape of applied stress. The hypothesis is that no particular strain shape is "preferred" in nature. Recall that FIG. 7 illustrates the range of strain shapes.

Figure 11:
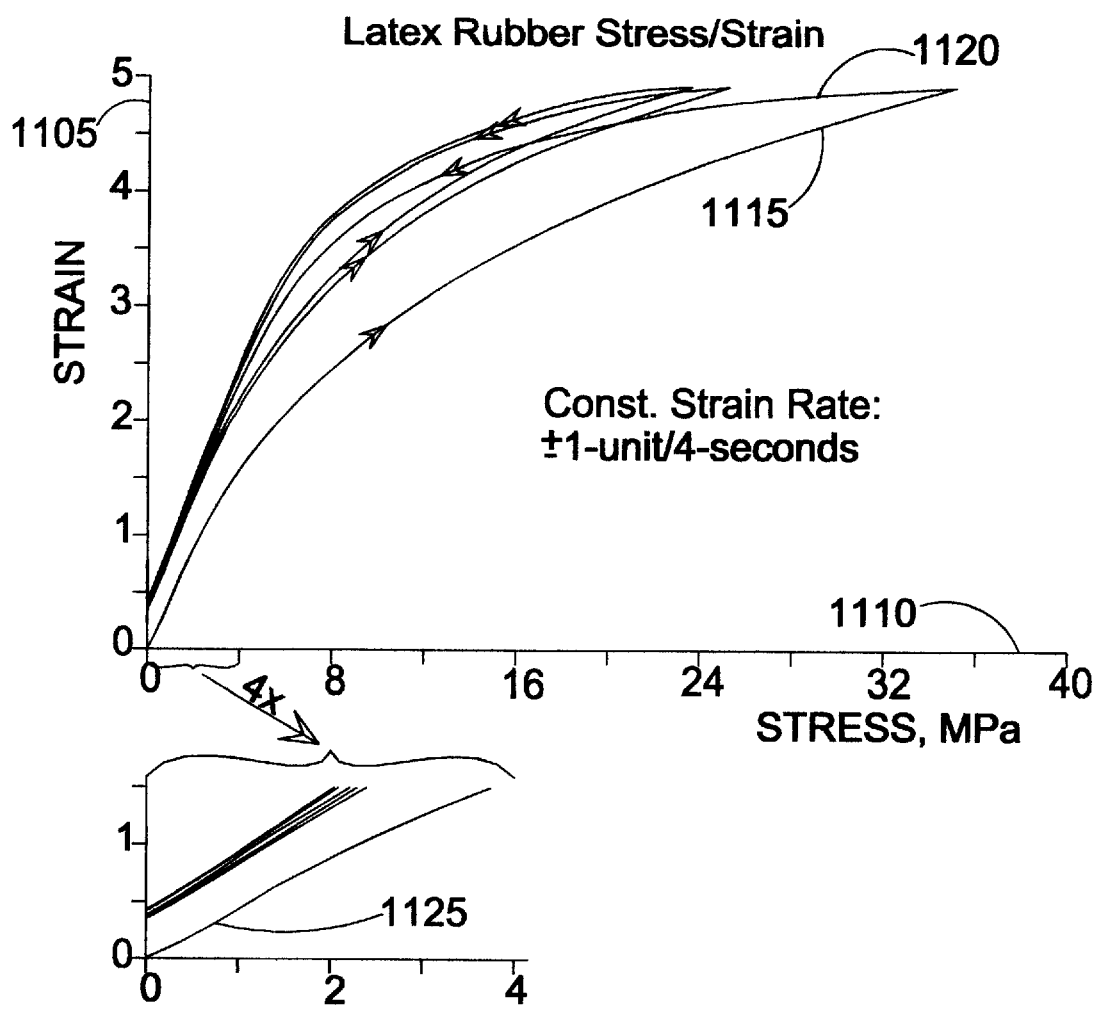
FIG. 11 illustrates stress over a time-varying cross-section of latex rubber subjected to periodic cyclic strain, illustrating characteristics of hysteresis, saturation, and possible evidence of a nonlinear hysteresis threshold phenomenon at the start of the plot.
Figure 12:
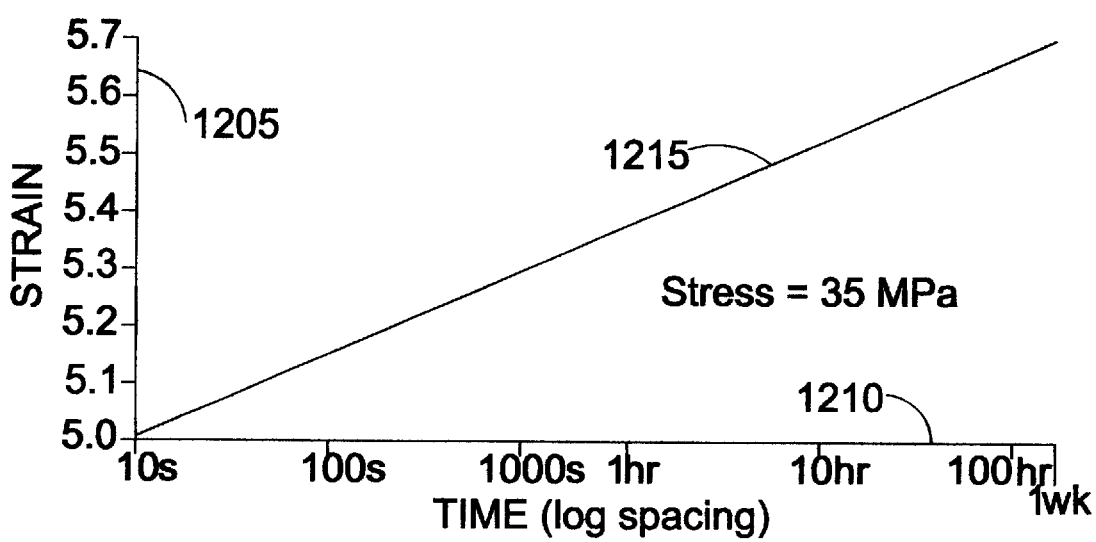
FIG. 12 illustrates a straight-line increase in strain when plotted against time on a logarithmic scale, under conditions of constant stress and temperature, for a similar latex material to that associated with FIG. 11.

FIGS. 11 and 12 illustrate dynamic stress/strain data for a grade of latex rubber, with stress plotted horizontally along axis 1110 and strain plotted vertically along axis 1105. The trace in FIG. 11 shows hysteresis between rising and falling portions (for example, 1115 and 1120) combined with progressive creep as strain imposed by the testing apparatus follows a triangle wave pattern of constant strain-rate ramps, varying cyclically up and down between zero and five (that is 500% elongation, stretching the rubber sample to 6 times its original length). The systematic decrease in slope of the curves at high strain is a saturation characteristic in the model of the present invention. The hysteresis is explained by the rate equation.

While stresses are normally plotted as force divided by the original unstrained cross-section of the material, stresses here are plotted as force divided by the corrected cross-section of the strained material, approximating pure shear strain at constant volume, equivalent to a Poisson Ratio of 0.5. (This trace was derived by the inventor from reduction of data provided by employer IMED Corp., the data being obtained using a testing device by Instron.) Plotting with this area correction, the beginning of the strain history curve, starting from the origin, suggests a slight initial increase in slope (along magnified region 1125) followed by a subsequent decrease in slope for most of the curve up to reversal. (Plotted without the area correction, there is a much larger apparent increase in slope starting from the origin, but this larger increase is an artifact of increasing stress concentration over the decreasing cross-section. If the Poisson Ratio is realistically assumed to be slightly less than 0.5, for example 0.49, then the increase in slope is easier to discern.) This increase in slope might not reliably be inferred from the data presented, but an independent experiment suggests that the increase in slope is real.

When similar latex material was used (in an experiment by the inventor) as an elastic band with a magnet serving as a weight suspended on the end of the band, bouncing motions of the weight were measured using a coil of wire as a velocity transducer. As the amplitude of vertical motion of the weight damped out, the oscillation frequency was observed to rise slightly but continuously with decreasing velocity amplitude. This oscillatory characteristic, and an increase in the slope of strain versus stress for the start of the stress/strain curve, are both consistent with nonlinear hysteresis in the domain model. Specifically, the material is stiffer for very small stress changes, with stiffness decreasing for larger stress changes because of an increasing value of RATE from Eq. 8 at increased stress, the increase varying across different types of domains in the representation of the rubber. At higher strain, saturation effects reverse this trend toward increasing slope.

FIG. 12 illustrates strain plotted on linear axis 1205 against time on a logarithmic horizontal spacing of axis 1210 at constant stress and constant temperature for a similar Latex sample, based on an experiment by the inventor. To within experimental accuracy, strain on a linear scale increased as a straight line 1215 when plotted against the logarithm of time from 10 seconds to one week after the initial application of stress. (The plot is exactly a straight line based on data, and probably fails to reflect real changes in slope that would be resolved by better data.) A linear log plot of this sort indicates that the domain energy barriers characteristic of the rubber are distributed uniformly over a range of energies for most of the domains undergoing strain transitions during the plotted test interval. A change in slope of the linear-versus-log plot would be symptomatic of a combination of two domain population phenomena: saturation of domain populations with increasing alignment toward the prevailing stress; and nonuniformity in the distribution of energy barriers over the range of barrier thresholds being revealed by the test. The detailed domain model presented here can resolve domain population distributions from data of the sort illustrated in FIGS. 11 and 12, or from data of the sort illustrated in FIG. 10.

Figure 13:
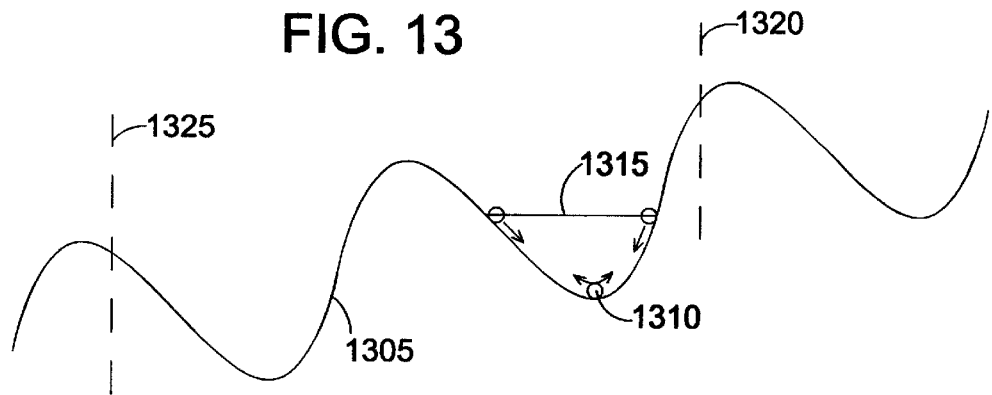
FIG. 13 illustrates an infinite periodic strain transition domain model subject to shear stress. The model is applicable to liquids and as a liquid component in a viscoelastic solid.

A third qualitative domain type was mentioned. In highly compliant and visco-elastic materials, a given domain transition becomes the precursor for a different transition that would have been impossible before the precursor transition. Thus, one can imagine extending the model to include strain transition domains with multiple potential wells. At the extreme of purely liquid behavior, the string of concatenated potential wells becomes an infinitely extended periodic function of energy peaks and valleys. As illustrated in FIG. 13, external stress tilts this wavy function 1305, promoting state transitions from one well to the next and then to the next, with total strain being unlimited. In terms of governing Eqs. 7 and 8, the equilibrium stress-strain balance curve of Eq. 7 does not apply to liquids—there is no equilibrium strain for a given stress, but only a rate-of-change of strain, that is, a shear rate. That rate is described by the variable RATE of Eq. 8. More specifically, the net shear rate, as a function of shear stress, is given by a weighted summation over equations of the form of Eq. 8, summing over distributions of energy barrier heights and stress coupling factors involving strain displacement volumes, shapes, and axis orientations in space.

The domain virtual particle of FIG. 13 is illustrated as a virtual particle 1310 oscillating back and forth in one of the potential wells of a periodic potential function at a total energy represented by line 1315, waiting to receive enough thermal energy to kick it over the barrier to a waiting lower well or, with less probability, to a well at higher potential. The continuous row of waves is slightly misleading, however, since it suggests that if the particle gained enough energy to go one well downhill, it would keep on going, gaining speed. The well illustrated downhill on the left below the vertical dashed line 1325 does not exist in the same dimension as the well with the number 1305, uphill on the right of line 1325. Similarly, the uphill well to the right of the dashed line 1320 on the right of the particle occupies another dimension, that is, a different degree of freedom of the system, whose thermal kinetic energy is independent (or nearly so) of the energy for the transition illustrated as one hop uphill.

In a deeper sense, the well located two dips downhill from the particle does not exist until the virtual particle has moved to the adjacent well located one dip downhill. Only then does the molecular configuration exist that can support the next strain transition. Furthermore, the available potential jumps are irregular from one to the next, like binary transition domains randomly selected from a distribution like that illustrated in FIG. 5. The wavy periodic function serves merely as a simple graphic reminder that the molecular configurations in a liquid can undergo an unlimited number of successive strain state transitions. When one transition is taken by a virtual particle, the reverse transition remains, and the particle can go back. When a second transition is taken, involving at least some of the atoms or molecules involved in the first transition, and along another axis in the 3n-space of an n-particle liquid, then going all the way back to the state of two transitions previous is extremely unlikely, since the two transitions must be retraced in the same sequence before some other strain rearrangement has erased the conditions that permitted the two-step reversal. Thus, with multiple strain transitions, shape memory is rapidly lost, both on a macroscopic scale, and also in terms of the chances for microscopic configurations to reappear through backward transitions that exactly undo forward transitions.

The viscosity model depends on the size of groupings of molecules temporarily sticking together, then being disrupted and rearranged by thermal agitation. As with strain transitions in solids with the binary domain model, a single particle will usually be locked in by neighbors, unable to move except in relation to the movements of others. Likewise, very small groupings of particles tend to be stable. If there are major gaps or strains permitting large downhill energy transitions, those possibilities quickly disappear, and one is left to seek ways that particles can rearrange themselves to produce small downhill energy hops following the direction favored by external stress. In larger particle regroupings, the possibilities multiply rapidly for complicated rearrangements that close some small gaps while opening up other small gaps with a near balance of energy changes, resulting is a small potential difference between the "wells" that represent the beginning and end points of a complicated strain transition. As the groupings for rearrangement become larger, however, larger numbers of molecules need to be pried loose from at least one neighbor, as illustrated in the simplified model of FIG. 4. In that two-dimensional chain dislocation, each overlapping polymer unit goes temporarily from having two adjacent neighbors to just one. In a dislocation involving a planar slippage, molecules in one plane may go from having three neighbors in an adjacent plane to just two neighbors midway through the slippage. This loss of attracting neighbors by each unit contributes cumulatively to the strain transition energy barrier, thus inhibiting thermal boosting of transitions for very large groupings.

If larger groupings represented proportionately larger strain volume displacements, then the shear energy coupling would go up roughly in proportion to the energy barrier. This is not the case, however. The net strain displacement of a molecular rearrangement does not rise in linear proportion to the number of particles significantly affected. Only the shape change that perturbs a distant surrounding sphere into an ellipsoid "counts" in terms of interaction with a "global" external stress field. More complicated or "higher order" shape changes attenuate rapidly with radius and thus to not "reach out" to interact with global stress. Another way to express this is that the more complicated shapes do not correlate with the simple shape of a strain ellipsoid. Hence, very large particle groupings hang together to resist thermal agitation and external stress, due to a "strength in numbers" of molecular bonds that contribute to the strain transition energy barrier. Very small particle groupings cannot easily regroup because they do not have enough "complicated" ways to achieve small energy transitions, while large energy transitions rapidly become unavailable and are not easily provided with the energy for their recreation.

Thus, there is a natural size range for the number of particles involved in a strain transition of the type that interacts strongly with an external stress to promote shear motion. The statistical model described above does not concern itself with the physics that determines that size range, but instead gathers data on the mechanical behavior implied by that size range, and by the energy barriers, and by the strain energy couplings, regardless of deeper underlying causes. Looking a little farther into the underlying physics, it is believed that the regroupings in liquids of small molecules involve fewer particles, on average, than the regroupings in polymers, either in the melt or solid state. A monomer unit in a polymer chain cannot move with the same degree of independence as a small liquid molecule, because the neighboring chain units are strongly constrained to follow the motion. The natural size for particle regroupings is expected to be consistently larger if the particles are mostly unit components of polymer chains.

The size of a regrouping, that is the number of molecules or units involved, is indicated by the ratio of the domain energy barrier size to the depth of a single potential well representing the molecular bond of two touching molecules or monomer units. The approximate size of a single potential well can be estimated from the potential well depth inferred from Van der Waals equation for a non-ideal gas. Based on a gas molecule similar to a polymer unit, for example, the Van der Waals coefficients for methane molecules are comparable to polyethylene chain units. The Lennard-Jones potential function is more realistic than the Van der Waals potential, and was used as the basis for the potential well shapes of FIGS. 1, 2, and 3, which were obtained by summing Lennard-Jones potential wells opening in opposite directions and spaced by the distance of the strain transition, in polyethylene, illustrated in FIG. 4. Where Lennard-Jones model data are available, use of those data is recommended over Van der Waals data.

To get a handle on re-grouping size in a simple liquid like water, the slope of the logarithm of viscosity as a function of temperature provides an indication. Specifically, a typical energy barrier height is derived using the assumption that viscosity varies as 1/RATE, where RATE is computed from Eq. 8. Using the approximation that viscosity is equal to a constant divided by the right side of Eq. 8, then taking the logarithm of both sides of the resulting equation, differentiating with respect to absolute temperature T, and multiplying through by $kT^2$, one obtains:

$$E_b = kT^2 \cdot \partial(\text{viscosity})/\partial T \qquad 9]$$

estimates energy barrier in liquid from viscosity

Dividing $E_b$ from Eq. 9 by the Lennard-Jones potential for pairs of atoms or molecules of a simple liquid yields an estimate of the number of such atoms or molecules that separate from neighbors to join new neighbors in a strain transition. For water, the result indicates that the effective number of simultaneous transient molecular pair separations is about 27 at room temperature, falling with temperature from about 32 near freezing to about 19 near boiling. This is an average figure for effective complete separations, from the minimum energy radius to infinity, though it gives an idea of the number of particles typically involved in a strain transition. By further steps, one can obtain a very rough estimate of the displacement volume typically involved in a domain transition, leading to an estimate of the nonlinear threshold for a significant reduction in apparent viscosity.

To get handles on regrouping sizes in polymer solids, one needs more complete models. The slope of strain at low stress, plotted against the logarithm of time at a fixed temperature, translates into an approximate plot of probability density as a function of energy barrier height—it's simply a matter of re-naming the axes of the same plot. Similar information can be obtained much more quickly by increasing temperature as strain data are obtained, in which case the plot of creep versus temperature is similar to the plot of the logarithm of viscosity versus temperature.

The degree of certainty of some speculations being made here does not affect the present utility of the domain model. This model provides a means to reduce macroscopic measurements to meaningful parameters that feed back into simulations, regardless of the detailed microscopic physical interpretations of the parameters. These glimpses into underlying physics do, however, suggest that stress/strain testing and viscosity testing, over ranges of temperatures, will provide data useful to the polymer chemist of the future, in understanding and controlling chemical processes, both on the time scale of human learning and on the much shorter time scale of process control feedback.

The invention described here, namely the domain model, coupled to means to fit model parameters to macroscopic test data, and the two of these coupled to a testing method and apparatus, becomes by logical extension a means to control and correct chemical processes whose outcomes are measured as mechanical properties and reduced to meaningful domain population distribution parameters.

In fluid viscosity, the frequency of strain rearrangement defines the lag between a changing imposed shear strain and the stress relaxation of domains, relieving the accumulating stress and limiting its average level. Eq. 8 is applicable to very high rates of thermally-driven strain relief for describing viscosity in a liquid, using the periodic domain model. While Eq. 7 describes the saturation limit of shear associated with the RATE of Eq. 8 for polymer solids, the saturation constraint of Eq. 7 goes away for liquids. There is no upper limit for shear strain in a liquid. Thus, Eq. 8 applies to viscosity while Eq. 7 is not part of the liquid model. A liquid subject to a shear rate-of-change is considered as an elastic solid in which stress is accumulating everywhere at a rate given by the shear rate-of-change multiplied by a shear modulus. This accumulation of stress is being relieved by domain transition events, limiting the average time for shear stress buildup to a value equal to a constant divided by RATE, where the constant is between 1 and 3. If the shear rate is very high, raising the stress in the shearing liquid to a high level, then the nonlinear character of the viscosity is manifested by an increase in RATE according to Eq. 8. Thus, this viscosity model is seen to have a nonlinear character such that increasing shear stress causes a nonlinearly increasing rate of strain. Looking at it another way, viscosity appears to decrease at high strain rates. This phenomenon is reported for polymer resins but is difficult to observe in simple liquids, due to a requirement for extremely high shear rates and due to turbulence, which can be difficult to avoid at required high shear rates.

In an extended empirical viscoelastic model, ignoring intermediate domain types for simplicity, one combines a binary transition domain model with a periodic transition domain model, as just described for liquids, thus incorporating elements of liquid behavior into the model. Though the optional compromise of omitting intermediate domain types sacrifices accuracy for simplicity, it achieves useful results in characterizing some viscoelastic substances and non-Newtonian fluids, for example, bread dough, cake batter, silicone putty, partially polymerized resins, and plastics that melt gradually without a sharp phase transition between crystalline and liquid states. Obviously, such characterizations require more than the six parameters of the standard polymer model.

To model an anisotropic solid like tensilized mylar, stress-strain modeling software can be used to "process" an isotropic starting material by straining that material, heating the material slightly to anneal certain internal stresses, etc., in a process resembling the actual manufacturing process. The resulting model has the parameters of the original model, except that the internal memory of the material, embodied in the dynamic array of $S_{ijk}$ parameters, is reinitialized by the simulated pre-treatment.

Catastrophic failure mechanisms in a material have been mentioned above. It is not too difficult to add ultimate stress limits to the model, for example, where polymers break down, and this is considered here as a natural extension of the invention. Such a breakdown description would not be meaningful outside the modeling context already defined, which is needed to understand and predict the extreme deformations leading up to a failure point. Once one has defined an ultimate failure stress, however, one recognizes more specifically how the domain model implies different paths leading to that failure stress. There are, for example, nonlinear "brittle" paths to failure, and less abrupt "necking down" paths to failure. These different paths are implied by the domain model. At relatively high temperatures, thermal annealing helps even out stress concentrations in a material and can lead to toughness. Higher temperatures reduce strength as creep becomes excessive. Lower temperatures can also reduce strength, as the thermal annealing effect is lost. Consider a sample that is being drawn in plastic deformation to high strain elongation. As the cross-section is reduced, tensile stress becomes more concentrated across the smallest area, which can lead to a rapid necking down with regenerative stress concentration, a path to failure.

At a lower temperature, the failure can be qualitatively different, as described earlier. If the material is cold, or if the strain rate is high, then stress at some region of the material reaches the nonlinear threshold where strain rate increases very rapidly as a function of increasing stress. The rapid strain in this region unloads the stress there, transferring the stress to an adjacent region, which subsequently enters the nonlinear region of falling stress. Quickly, the entire cross-section begins to stretch rapidly across a thin layer, allowing the material on either side of the failing layer to begin to rebound elastically, further increasing the strain rate in the stretching layer and preventing the stress there from falling. This regenerative process is a path to failure across an entire cross-section, ending in rupture with little necking down. Variations on this theme occur where an impact imparts concentrated stress abruptly and the material shatters. The domain model permits quantification of this sort of brittleness, leading to detailed analysis of the events leading to rupture, whether or not the model is endowed with parameters that describe the final stages of the rupture process. From a practical viewpoint, the final details of failure are often of only academic interest if the model clarifies the conditions for approach to a recognizable condition of catastrophic failure.

The domain model described here has not been extended to analyze fatigue, although some properties of the model suggest mechanisms that might be related to fatigue. This interesting area awaits further extension and sophistication of the model described above.

Summary, Component 2—Method and Means for Data Processing:

Because the model described above can not be extracted from the test data directly, as is the conventional case where chart recorders simply log, for example, force vs. displacement, this invention requires a method of computationally manipulating the data to develop the parameters of the model. Several modeling variations have been described, involving polymers, metals, and viscoelastic materials, typically calling for between four and eight independent parameters to be resolved from test data. Fitting these parameters to empirical test data calls for a functional minimization procedure. Such computational procedures are very well known and well studied, so a brief description will indicate how they work in this particular context. The dynamic simulation model is used, with an initial estimate of the parameters, to simulate all the empirical tests performed on one or more material samples. The nature of such tests will be discussed below. The result of testing and simulation is paired "families" of time-domain response curves in stress and strain: the reference measured curve and the parameter-dependent simulated curve. An error function is defined, for example, a weighted sum of the squares of differences between points of measured data and points of simulated data.

The weighting factors are a matter of priorities: regions of behavior which are most important, calling for the best fit, are weighted more heavily. Regions subject to experimental error or other uncertainty are typically weighted less, to prevent them from spoiling the model for important regions.

The resulting scalar error function is to be minimized with respect to variations in the free parameters, repeating the dynamic simulation with differing input vectors whose components are the free parameters of the model. Simple functional minimization procedures, such as the Simplex Method of Nelder and Mead, tend to be reliable but slow. A more complex procedure converts the scalar error into a vector error, consisting of the partial derivatives of the scalar error with respect to each of the components of the free parameter vector. The objective is then to drive all of the components of the partial derivative vector to zero simultaneously, which occurs when the scalar error function has been minimized.

This simultaneous minimization of the vector components may be approached by a vector-matrix version of Newton's method, for the number of dimensions involved. This approach may be unstable and fail to converge from large errors, requiring more elaborate procedures, many of which are commonly known. The advantage of these vector methods is that they may require far fewer simulation runs in order to converge to a best-fit set of parameters.

When the process is finished, one obtains a mathematical model of the material whose mathematical responses usually fit the observed data well and can be extrapolated well beyond the realm of observed conditions.

Summary, Component 3—Means for Influencing the Sample and Obtaining Test Data:

To obtain the set of data required to compute the model from the specimen, the invention demands a novel testing means and apparatus. Choosing the means for measuring and obtaining test data requires some knowledge of the range of conditions needing to be probed by the tests, as is now examined. To first consider binary strain transition domains, we observe that for a given domain type, one needs to resolve the energy barrier height, the intrinsic bias of the energy differential at zero external strain, and the strain displacement volume, which along with geometric factors determines the coupling strength between external stress and the energy differential between the potential wells. Data at low stresses and at increasing temperatures will reveal absolute heights of energy barriers. At a given temperature, the small-perturbation linear equilibration time for a domain is roughly exponentially dependent on the ratio of the energy barrier height to the characteristic thermal energy, kT. This settling time at a given temperature can vary from microseconds to millennia. If a stress is applied very abruptly and strain data are obtained very soon after the stress is applied, the test reveals the character of fast-settling domains, knowledge which is needed to characterize impact strength and brittleness. Reducing the temperature slows the equilibration process, allowing one to extend the measurement resolution to lower energy barriers by slowing down processes that are otherwise too fast to observe in a simple apparatus.

Conversely, the highest energy barriers are revealed by the slowest equilibration behaviors. One resolves information about very high energy barriers by raising the temperature, bringing very slow processes within measurement range. Thus, with a single sample of material to work with, an effective approach for resolving energy barriers is to apply a low stress abruptly at low temperature, take very frequent strain measurements at first, then less frequently as the process slows down. To keep things moving, one can heat the sample, monitoring and recording the temperature and assuring that the sample never moves too far from thermal equilibrium with the temperature measurement system. The data from the maximum time interval at the maximum temperature will reveal the most about high-barrier domains.

Once the energy barrier information is resolved, larger stresses applied at lower temperatures will reveal stress energy couplings, that is, the domain displacement swept volumes, as the applied stresses couple to the domains sufficiently to overcome the energy barriers with less thermal "help." Saturation behavior is observed when domain populations are all pushed into the same tensor "direction," resolved along the axes of applied stress. While high stress levels reveal saturation behavior, they also threaten to push components of a sample into failure, potentially causing rupture or internal breakdown, for example, breakage of polymer strands, before the non-failure characteristics of the material are fully revealed. Samples need to be pushed to failure, some of them starting at low temperatures and with stress increased gradually, allowing the material to be drawn out and exhibit its maximum strength before failure.

Wide-ranging tests as described will bring out the spread of intrinsic stress bias, which should manifest itself through spreading out strain responses over a wider range of stresses. Thus, behavior will appear more linear, both with respect to saturation and with respect to nonlinear strain-rate thresholds, if there is a wide spread of intrinsic bias. To further emphasize intrinsic bias in experimental data, however, stress should occasionally be relieved, since the shape of elastic recovery is a strong indicator of intrinsic bias distribution, which is not so readily resolvable from data with steady or monotonically changing stresses.

Temperature cycling will result in reversing cycles of strain increase and decrease, superimposed on a general trend of strain increase at sustained stress due to creep. These reversing temperature cycles will reveal more about the relationships whereby rising temperature drives domain equilibrium strains "S" toward zero as domain states tend to be randomized by thermal agitation, while falling temperature drives the same equilibrium strains away from zero at constant stress, and further toward saturation. While the competing thermal effects of shifts in static equilibrium strain and shifts in the dynamic rate of settling toward equilibrium may confuse our conceptual picture of this complex dynamic, the domain model will readily resolve these overlapping effects. A good testing protocol should include periods of stress application and stress relief, and of heating and cooling, with some of the stress relief periods coinciding with heating periods, others coinciding with cooling periods, testing all the combinations.

Backing off and examining what has just been described, these types of testing protocols differ significantly from conventional materials testing. In characterizing creep modulus of a plastic by earlier techniques, a constant stress is applied at a constant temperature, and no measurements are taken until (typically) one hour after stress application. The early strain data, from one hour down potentially into the millisecond region (limited only by the speed of the testing apparatus), is valuable but not used, possibly because there has been no way to interpret it., Cyclic variations and step variations in stress, and cycling of temperature, are not included, presumably to keep the complexity of the data manageable. Separate tests are performed on separate virgin samples, because there has previously been no computational model for analyzing the effect of a complex stress history on a single sample. Fast behaviors are probed by impact tests, with no theory or models telling how to bridge between impact data and creep modulus data.

With the model described herein, and a method of matching the model to empirical data, one is encouraged to subject a few virgin samples, or possibly just one sample, to a complicated history of stress and temperature, including rapid step changes in stress, applied in combination with different prevailing temperatures at different stages of the test. The model and the parameter-fit process extract from the complex data a comprehensive description of the material. The testing procedure no longer attempts to isolate different aspects of material behavior through separate simple tests on separate virgin samples.

As a practical matter, tensile stresses are commonly easier to apply for strain measurement than compressive stresses, because a long sample, for example a fiber, can be drawn to high stress with little applied force while elongation is measured over a long length, but of course such a long thin sample will buckle before it supports much compressive stress. Bending stress is more complex to analyze and simulate, involving varying levels of compression and tension in different parts of the sample. The theory of shear strain described earlier suggests that the shear aspect of compression is simply another symmetry for shear. If nature does not prefer one shape of strain transition domain to another, then tension data should reveal the same basic information as shear data. Data to determine model parameters can be obtained from tensile elongation data for a thin object, and the resulting model predicts behavior for two-dimension stretching, for example, in the shear strain symmetry of the surface of an inflating balloon.

The only limitation of these comparisons is where negative compressive stress becomes a significant effect, bringing out another dimension of material behavior. In hard materials, with Poisson Ratios on the order of 0.3, the compressive modulus is important. Negative compression can be high in comparison with the magnitude of shear stress, and failure of a material can be very dependent on the scalar pressure component of stress. In elastomers, a common Poisson Ratio is about 0.49, implying that shear strain dominates strongly over change in volume in a tension test. It is believed that polymers, and more especially elastomers, are far more affected by shear stress than by positive or negative scalar compressive stress, such that the negative compressive stresses associated with tension tests are expected to be relatively unimportant. The tests described here probe shear properties using tensile stress, which combines shear stress with negative pressure. Where the negative pressure has little effect, the shear stress result applies to any strain geometry. In harder materials with lower Poisson Ratio values, tensile testing may not apply as accurately to compressive loading.

Seeking a testing apparatus and test protocol based on the above considerations, for quick testing one wants a few matched samples to test simultaneously at varied stress levels, from low to high. In a reasonable simplification, the strain tests can all begin at once, since rapid data collection from multiple stress or strain sensors is easily achieved. In a preferred testing embodiment illustrated in FIG. 14, and described more thoroughly below, arrayed springs are pre-stretched and their tensions supported mechanically, after which the tensions of the springs are transferred abruptly from each spring to a slender material sample. If the spring lengths change only slightly as the mechanical support is removed and tension is transferred to the sample, then transient shock and vibration are minimized. The goal is to achieve a quick, step-like increase from a low pre-tension to a near-constant higher tension in each sample. Subsequent strain of the sample is then measured by any of several linear measurement techniques, for example, optically by video or by 1-dimensional photodiode arrays. When tension has been applied to all the samples and strain measurements are being taken on them all, then temperature is raised progressively over the duration of the measurement period. As time progresses, samples are periodically unloaded, so that their elastic recovery can be observed for a period, after which the samples are again loaded with the constant spring force. A single actuator can unload and reload all the test samples at once.

For some tension recovery periods, the temperature of the enclosure is lowered briefly, revealing the effect of temperature decrease, then revealing the effect of tension decrease at both high and low temperatures. After each temperature reduction, temperature is brought back up to the previous level, following which an increasing temperature ramp is resumed into a new, higher range. Excepting for cooling interruptions, the temperature ramp is caused to go high enough that samples at differing tensions will begin to fail partway through the testing period, the samples at the least tension failing last or not failing at all by the end of the test.

It is also recognized that pre-existing test data can be used to resolve the parameters of a stress/strain model. For utilizing such available data, means are required for reading, storing and importing the data into the software system described earlier. Where graphical or printed data are presented, various devices for digitizing hard-copy graphical data can be coupled to the software system to bring in the data. For example, a cursor can be moved over the axes, scale marks, and graphs of creep-modulus data families. That cursor can be a device moved across a page while its position is measured, or it can be a computer cursor moved across the pixels of a scanned image on a screen under human operator control. Appropriate software may be devised to automate the conversion of a scanned graph into tabular data. Where data are available in digitized tabular format, a digital data transfer device, be it a modem or disk drive or network cable or other means, becomes the data source for bringing in the data to be reduced in this novel way, recovering parameters of a detailed dynamic description of the material that could not have been contemplated when the data were originally gathered.

One might say that a new use has been discovered for pre-existing raw data, that use depending on the software system and method of data processing that has been described above.

DESCRIPTION OF A PREFERRED EMBODIMENT

The preceding summary has been fairly comprehensive, implying a range of possible embodiments. The stable core of these embodiments is an original physics analysis and computational method for obtaining a meaningful and accurate approximation of complex, nonlinear, temperature dependent dynamic stress/strain responses in a wide range of materials, particularly polymers and elastomers. The invention becomes more complex when it comes to methods for error minimization to obtain an optimum parameter fit to data, with a number of preexisting methods being adaptable to the completely new context described. At the data acquisition end of the system, the possibilities take on the broadest range, with many sets of tests that probe the range of material properties being applicable. Impact and scratch or hardness tests do not probe such a range, but creep modulus tests do better. Those tests do not anticipate the utility of much shorter-term data, which can be used to broaden the range of model validity. Thus, the preferred embodiment to be described here includes a testing device that imposes nondestructive stresses quickly, obtains time-domain response to high resolution soon after the stress application, and then extends the testing over a longer time period at increasing temperature, as described in general terms above. What is to be described next is a specific structure, indicative more generally of the type of device that affords a means for exploring a broad range of material parameters and characteristics with high speed and low complexity.

Figure 14:
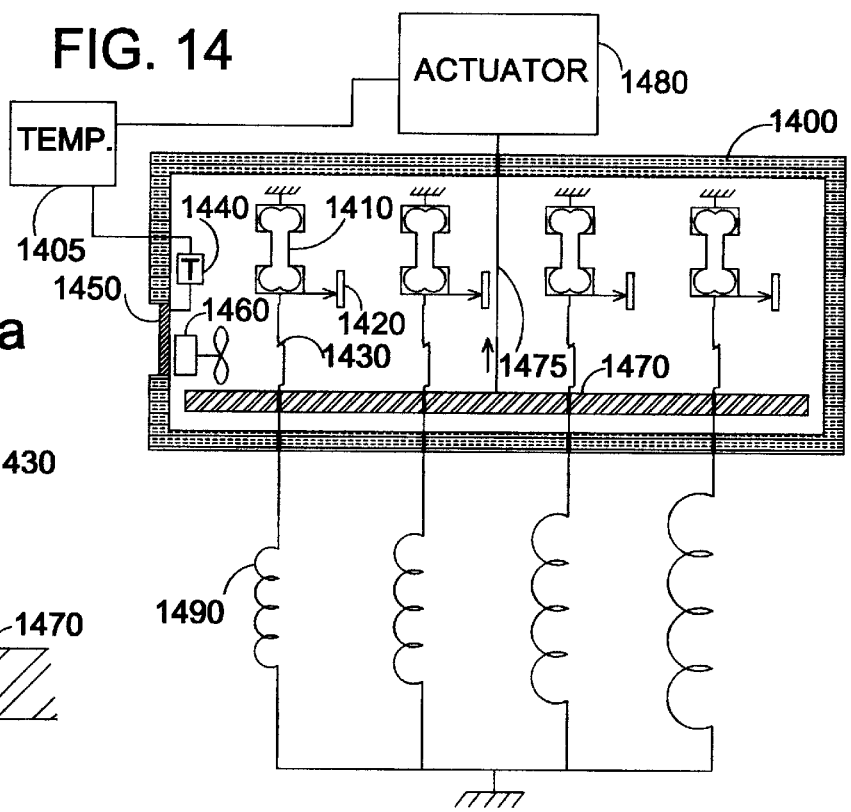
FIG. 14 is a sketch of a preferred embodiment of a material testing device utilizing principles of the invention, testing several material samples at once at varying temperatures and with forces that are applied and removed abruptly to elicit high frequency response behaviors.
Figure 14A:
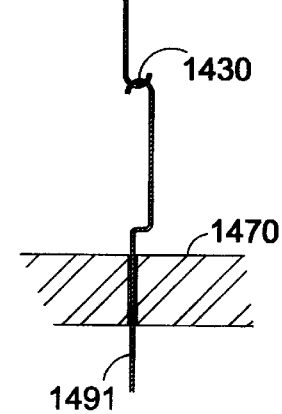
FIG. 14a is a magnified view, from FIG. 14, of a mechanism to couple and decouple forces between springs and material samples, with the mechanism illustrated in the coupled position.
Figure 14B:
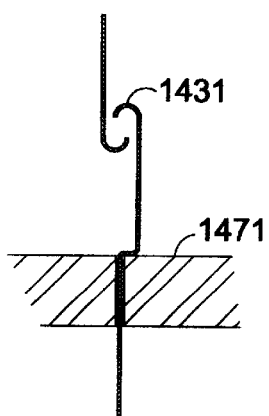
FIG. 14b is similar to FIG. 14a but shows the same mechanism in the decoupled position.

Because the set of data to be taken may require, in any combination, abrupt, gradual and reversible applications of force, displacement, temperature and other perturbing variables, it is expected that the testing apparatus provides means for both applying these influences and for monitoring their instantaneous value, as well as means for measuring their effect on the material sample. As illustrated in FIG. 14, a row of tension springs of varying strengths, such as spring 1490 on the left of a row of springs of increasing predetermined strength, is provided to apply differing, fairly steady tension forces to a row of material samples 1410, shown for example, in the traditional "dog bone" shape that permits easy grasping of the material sample in order to stretch it. A linear actuator 1480 moves a bar 1470 that engages or releases all the springs. As drawn, the upper spring ends extend upward through small holes in insulating box 1400 and through small holes in bar 1470 to hooks that engage, at coupling points 1430, to the lower ends of the samples. Detail FIG. 14a better illustrates the upper end 1491 of spring 1490 extending through the small hole in 1470 and engaging the sample via 1430, which is a pair of hooks that engage or disengage. The hooks are shown engaged at 1430 in both FIGS. 14 and 14a, while the same pair of hooks is shown disengaged at 1431 in detail FIG. 14b. The bar 1470 is shown lowered in FIGS. 14 and 14a, while the same bar is indicated, at 1471 of FIG. 14b, raised to take up the force from spring 1490. Raising of the bar thus permits the disengagement at 1431. This raising of bar 1470 is accomplished by actuator 1480, as indicated in FIG. 14 by the upward arrow on the line 1475 between the centers of 1470 and 1480. This line 1475 is mechanical means such as a rod to raise or lower bar 1470. Summarizing, each spring is coupled to its material sample by an engagement mechanism 1430, which transfers tension but decouples so as not to transfer compression, in the same manner as a hook. When linear actuator 1480 pulls bar 1470 via 1475, this bar presses on the spring-coupled ends of the engagement mechanisms 1430, causing them all to decouple from the samples. When linear actuator 1480 lowers bar 1470, this action disengages mechanisms 1430 from the effects of linear actuator 1480 and allows tension from each of the springs 1490 to be transferred abruptly to the corresponding material samples 1410. The springs 1490 move only a minimum distance between engagement and disengagement with the samples 1410, so that the spring tensions are transferred to their samples 1410 rapidly, but not too rapidly, and without significant motion or impact.

Elongation of each sample is measured by a strain measurement device 1420, its measurement of position symbolized by a pointer moving along a scale. This device may, for example, be an optical linear encoder; for materials with high strain, such as rubber, a good strain measuring device is a quadrature Moiré encoder., For materials with low strain, an optical interferometer is a good device. Though many options are available, one requirement is that the strain measuring device must have low offset drift with temperature changes in the measurement chamber.

A heating and cooling means 1450, for example, a thermionic device, is provided for altering and controlling the temperature of the samples, where necessary augmented with an air circulation fan and motor assembly 1460, and a temperature sensor and thermostat assembly 1440, which is connected to the heating and cooling means 1450. The testing area is preferably enclosed in an insulated box 1400, with a connecting rod 1475 passing into the box from the actuator 1480 to the bar 1470. The springs are similarly coupled by their upper ends 1491 passing into the box from the exterior portions of springs 1490, so that large temperature fluctuations in the box do not affect the springs. Control device 1405, for example, a computer, connects to sensor/thermostat assembly 1440 for control and measurement, connects to actuator 1480 for control, and receives measurement input (connections not shown) from the strain measurement devices 1420.

In a preferred testing protocol, to be controlled by device 1405, the samples are set in place, not under tension, with the springs pre-stretched and ready for transfer of their forces to the samples. Data acquisition is begun on all the strain sensors, and temperature is thermostatically lowered to a minimum value for the start of testing. Spring loads are transferred to samples, providing forces that are known, as functions of the strain position readings, by prior calibration of each spring with a single load cell. The data acquisition system monitors the samples continuously to detect the onset and progress of strain in each sample. When such an onset is detected for any sample, strain data are recorded very frequently at first, to capture in detail the first fractions of a second of strain motion. If differing samples do not engage or disengage with their springs at the same time, for example, due to differing strain elongations, the data acquisition system nevertheless detects the times that the various samples experience the transient of loading or unloading.

The frequency at which instantaneous sample influence and response data are recorded and stored may be reduced when rates of change are slow. Conversely, on initial loading or unloading of a sample, the data acquisition system takes and retains a flurry of readings where motion has been detected. As discussed above, periods of heating and cooling should be applied and alternated so that both cool and warm periods coincide with periods of tension relief and tension re-application. With multiple samples of matching material coupled to different tension springs, there is no compelling reason to provide continuous variation in tensile stress on various samples—different samples exhibit the response of the same material to different levels of stress. These differing levels are alternately applied and removed, via the disengagement mechanisms 1430, to "exercise" the samples, revealing responses of both elongation and recovery. It is understood that variations on the embodiment described could alternately apply and remove compression, or both tension and compression, to a collection of samples of matched materials.

The preferred embodiment thus includes means for imposing known applied influences, such as temperature and stress, means for measuring responses of the sample under these influences, such as strain and changes in state, and means for performing mathematical calculations on these data to obtain a concise set of parameters which match a statistical mathematical model to the characteristics of the material under test.

Description of an Alternative Embodiment

The above device and protocol emphasizes parallel measurements on multiple samples for obtaining quick results. An alternate embodiment sketched in FIG. 15 uses more sequential measurements on a single sample at multiple stress levels. An actuator, for example linear actuator 1580, couples a variable force into an insulated box 1500, whose internal temperature is regulated via temperature sensor/thermostat 1540 driving heating and cooling device 1550, for example, a thermionic device. Fan and motor assembly 1560 helps maintain a uniform temperature in the box. Inside the box, actuator 1580 connects to load cell 1530, which in turn connects via a hole in the wall of box 1500 to the end of sample 1510. The end of 1510 connecting to 1530 also includes a strain sensor 1520. Controller 1505 connects to actuator 1580 for control, to load cell 1530 for force measurement, to temperature sensor/thermostat 1540 for temperature measurement and control, and to strain sensor 1520 for strain measurement. It is seen that, aside from a single sample versus multiple sample testing, the principal difference between this testing device and the multiple sample testing device described above is a design for a continuously variable, measured force applied to the single test sample, as opposed to a design for a single actuator to load and unload multiple samples which simultaneously experience either no load or a fixed load that varies from sample to sample. It is, of course, possible to devise a system with multiple actuators for independent, continuous control of force on multiple samples.

Figure 16:
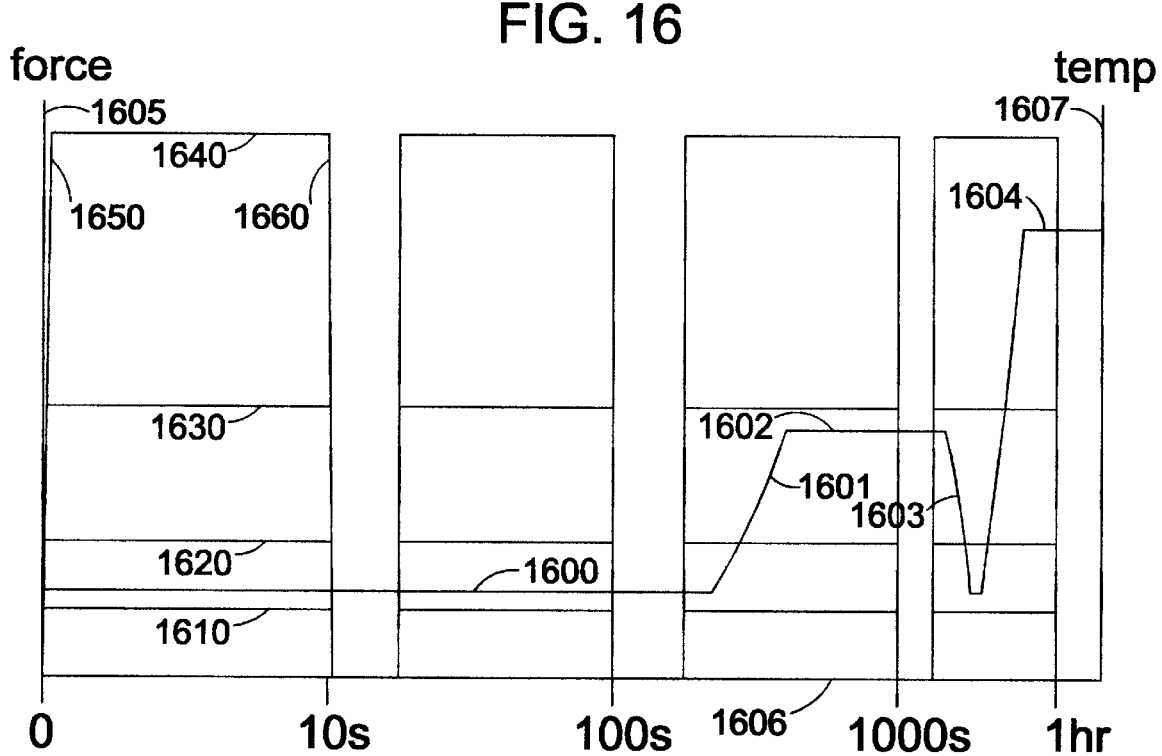
FIG. 16 is a plot, against time on an approximately logarithmic scale, of temperature and of forces exerted on material samples, illustrating testing to reveal dynamic material properties.

While prior testing devices and methods sought to start each new test with a virgin sample, preferably matched to other samples used in related tests, the complex software model of the present invention sorts out the cumulative time-history effects on samples, as discussed above and further illustrated in FIGS. 16 and 17. FIG. 16 illustrates a testing procedure that can be carried out on an apparatus such as is illustrated in FIG. 14, with four nominally identical material samples subjected alternately to zero force and to four force levels, from a minimum level indicated at 1610 through higher levels at 1620 and 1630 to a highest level at 1640. A vertical scale on the left at 1605 indicates force, while a second vertical scale on the right indicates temperature at 1607. Time is plotted with approximately logarithmic spacing on horizontal axis 1606, except at the left end of the scale, where time goes to zero. As shown, force increases steeply along 1650, leveling off for the four samples at the four levels 1610, 1620, 1630, and 1640, for example, at the time when actuator 1480 of FIG. 14 releases bar 1470, transferring stress to the material samples 1410. Strain is subsequently measured with devices 1420 while, returning to FIG. 16, temperature is initially maintained steady along line 1600. Very frequent strain measurement samples are retained immediately after force application, to capture the transient response to the resulting stress in the samples, and similarly again after the force removal at 1660, shown here after a relatively short duration of sustained force, indicated at about ten seconds on the time scale. After some recovery measurement, force is re-applied to the samples for a longer period of time, for example, out to 100 seconds, then removed again for a recovery period. Temperature is then raised, along curve 1601, to a higher plateau at 1602, after which the sample is allowed to return to thermal equilibrium before another force removal, for example, at 1000 seconds, followed by a recovery period and reapplication of force. The curvature in the temperature graphs is intended to depict the distortion of a relatively straight-line temperature slewing when the time scale is nonlinear. After force is restored, temperature is lowered at 1603, to help reveal how the equilibrium strain in the sample shifts with temperature, even as the equilibration process may cause the net strain rate in the sample to continue against the direction expected on the basis of temperature change alone. Temperature is raised to a final plateau, the highest level, at 1604, and sustained for a relatively long time period (made to appear short due to the logarithmic time scale), until force is removed near the end of the test, for example at one hour. A final period of strain recovery may be monitored after the final force removal and before ending the test. This procedure is, of course, only one example among many possibilities, emphasizing several themes: abrupt force application and removal, a range of forces applied to different samples, a progression from short to longer time scales of sustained force, and an increase in temperature. The temperature elevation effectively stretches the time scale to reveal material behaviors that would otherwise be revealed only by a much longer test at a lower temperature.

Figure 15:
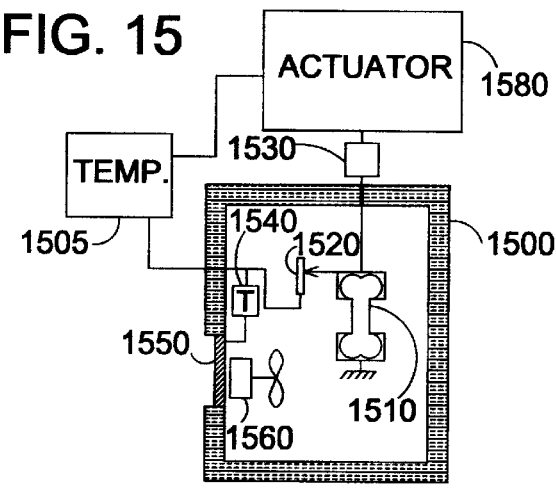
FIG. 15 is a sketch of a second embodiment for more involved testing of a single material sample with controlled time-varying forces and varying temperatures.
Figure 17:
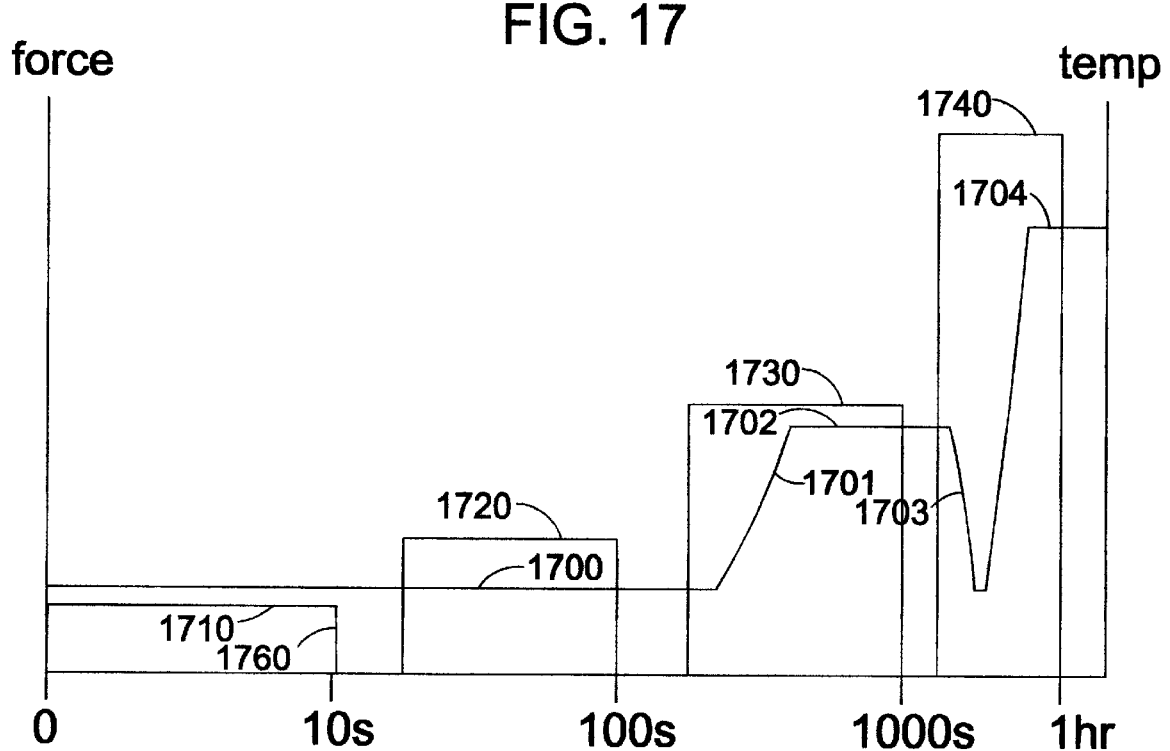
FIG. 17 is similar to FIG. 16, but showing variable force levels exerted on a single material sample instead of separate force levels exerted on separate samples.

FIG. 17 illustrates the time sequence of testing for a device like that shown in FIG. 15, applying different forces over time to a single material sample. The graph scales of force, temperature, and time are the same as for FIG. 16. In this case, however, a low force at level 1710 is initially applied to the single sample, with force removal at 1760, similarly to the removal of force 1610 at 1660. Temperature is steady at 1700. When force is re-applied for a longer duration, it is at higher level 1720. This force is removed, and then force is applied at a higher level 1730, which is sustained longer than at level 1720. To accelerate slow processes in the sample and collapse the effective time scale, temperature is ramped up at 1701 to a plateau for thermal equilibration before another stress removal and reapplication at the highest level, 1740, which is sustained for the longest period (recalling the logarithmic time scale.) As at 1603, temperature is lowered at 1703, allowing for a brief thermal equilibration before raising temperature to the highest level at 1704.

With an ability to analyze a sample that retains some state memory of the past history of applied stress and temperature, it is worthwhile to subject a single sample sequentially to a wide range of temperature and stress conditions, starting with conditions causing moderate strain and extending to conditions causing more extreme strain. While conventional dynamic testing protocols have applied smoothly varying cycles of stress or strain, the current analytic model suggests that stresses should be applied and removed abruptly, the better to reveal the complex time dynamic of a material. Abrupt application of strain, as opposed to stress, is an alternative but risks the creation of excessive stress and premature damage to the material sample.

The programmable device described in FIG. 15 for single-sample testing therefore incorporates a linear force actuator, possibly operating at a selectable mechanical advantage depending on the force magnitude to be applied, and operated in conjunction with a load cell to measure the force applied to the sample and a linear displacement sensor to measure strain in the sample. An actuator controlling imposed strain rather than stress, for example, a stepper motor coupled to a lead screw, can be controlled in conjunction with a force measurement device such as load cell 1530 to accomplish the same end. Thermostatically controlled heating and cooling are provided, as in the previously described device.

The testing protocol, in general, is to start with a cold sample and apply cycles of stress and no stress at increasing stress peaks, changing the stress in abrupt steps and concentrating retained data for the periods immediately following the step changes. The sample is then cooled one or more times, returning to increasingly higher temperatures, with stresses alternating high and low or possibly reversing in direction, depending on whether it is practical to subject a given type of sample to significant compression. The stress peaks should be reduced at higher temperatures, to avoid premature production of excessive or damaging strain magnitudes at high combined temperature and stress. To end the test, the sample may be brought to a stress and temperature combination that causes failure (not illustrated), which could be high temperature creep failure or low temperature brittle failure, depending on the desired emphasis of the testing.

A Variation for Magnetic Testing and Material Characterization

The most definitive parameters from the conventional way of characterizing ferromagnetic and ferrimagnetic (ferrite) materials have been saturation induction, coercive force, and the Curie temperature. While these parameters begin to describe flux density (B) versus magnetic force (H) curves, much more is needed for a complete characterization of dynamic responses to complex waveforms at varying temperatures. The statistical mechanical binary domain model described above for mechanical stress modeling may be modified for modeling magnetic materials.

It is known that some types of magnetic domains have more than two stable states, meaning that the material may have two separate "soft" axes of magnetization, allowing for + and − orientations with respect to two directions. It is also known that as an H-field is progressively applied, the revealed potential energy plot of an affected domain may be a complicated path having several local maxima and minima. Simplifying the representation of outcomes for such paths, a collection of binary transition domains may be used to approximate the behavior of a smaller number of more complicated domains. The resulting binary domains are not all symmetric, but exhibit a distribution of values for intrinsic bias, by analogy to the horizontal distribution spread illustrated in FIG. 8 for mechanical domains. In addition to a symmetric distribution with respect to bias, one characterizes the domain types according to barrier energy and according to a volume measure characterizing the magnitude of interaction with an external field, to alter the energy differential between potential wells. To an approximation, one can use mean values and dispersions to define distributions of domains over intrinsic bias, barrier energy, and volume.

On closer examination, one encounters other details of a magnetic domain model, some of them different from the mechanical model. There are differences in the one-dimensional domains themselves, and differences in how energy is coupled between domain transitions and an external field. Focusing first on the differing dimensions of interaction with the domain, the interaction energy between a mechanical transition domain and a stress field is the product of a domain volume times a stress, with a correlation factor COS. Stress has the dimensions of energy/volume, so multiplication by a volume yields an energy. In the magnetic case, energy is the product of (H-field)×(dipole moment density)×(volume). The dipole moment density is equivalent to a saturation B-field strength, which is a characteristic property of the magnetic material, regardless of domain sizes or arrangements or manufacturing processes such as heat treatment. This dipole moment density is insensitive to temperature well below the Curie temperature but declines steeply to zero at the Curie temperature, following fairly accurately and consistently a curve that is well known in magnetic theory. This temperature-dependent change in an intrinsic domain property has no obvious counterpart in the solid mechanics model, as understood to-date. The product of volume times dipole moment density is dipole moment, per domain. The dot product of this dipole moment with the external H-field is an induced energy differential between potential wells, which adds to the intrinsic differential. By contrast with this vector dot product, a mechanical shear strain transition domain has a volume transition, characterized by a volume magnitude and by a tensor shape, described in terms of a shear strain ellipsoid having a particular shape (one angular degree of freedom), a direction of the principal axis spanning solid angle (two dimensions of a spherical surface), and an additional rotational orientation about the principal axis (one angular degree of freedom). The shear strain transition domain description is thus five-dimensional (a volume magnitude, a shape, and three orientation parameters), whereas a magnetic dipole transition domain is three-dimensional (a dipole moment magnitude, and two orientation parameters). The coupling correlation factor COS of the solid model becomes $\cos(\theta)$ in the vector dot product model, where $\theta$ is the angle between the domain axis and the external H-field axis. In mechanics, a five-dimensional product yields a scalar energy differential, which acts along the one dimension or degree of freedom of the domain. In magnetics, a three-dimensional product yields a scalar energy differential, again acting along the one dimension of the domain. The one-dimension domains of the two descriptions are formally analogous, including excitation by an average thermal energy kT. The coupling bandwidth factors, BW, can be very different. At a detailed level, the two types of domains are excited or "vibrate" differently, in one case by magnetic precession, in the other case by vibration along an axis in 3n-space describing a particular set of correlated motions of molecular components.

The distribution function of the COS factor for isotropic material is replaced in magnetics by a distribution function of change of solid angle per unit change in the projection coefficient, $\cos(\theta)$, for off-axis coupling angle $\theta$. While the COS probability distribution as a function of magnitude from −1 to +1 is a bell-shaped curve flattening out asymptotically toward a horizontal tangent at either end, the normalized $\cos(\theta)$ probability distribution is a constant probability density of 0.5 over the interval $-1 \leq \cos(\theta) \leq +1$. Thus, there is a higher probability density in magnetics near the −1 and +1 extremes of the $\cos(\theta)$ probability distribution than for the COS distribution. For an anisotropic magnetic material aligned totally in the direction of the applied stress field, the coupling distribution function becomes a pair of spikes, or delta functions, each with an integral of 0.5, one lying at −1 and the other at +1. This case gives the least spreading of the strain transition response over a range of applied magnetic stresses—meaning, in this context, applied H field strength, also known as magnetomotive force. It is suspected that this minimum spreading case for aligned magnetic materials may not be observed in the corresponding solid mechanics theory, even for a highly aligned anisotropic material, if the distribution over shape in the solid mechanics model turns out not to respond to procedures like drawing a material as it polymerizes. This area is not yet well understood. Contrasted with the aligned anisotropic material, the constant probability distribution for isotropic magnetic substances gives a wider spread of responses in the "tail" of the saturation curve, where increasing H-field levels are needed to flip domains that are aligned more and more nearly orthogonal to the H-field. Thus, the saturation curve averaged over distributions settles to its asymptote slowly, for example, as the inverse square of H, depending on other distribution functions, rather than with the very rapid exponential or Gaussian convergence that one might expect from the other distribution functions involved. Where the solid mechanics COS distribution pushes more domain couplings away from the −1 and +1 extremes, this further reduces the slope of a curve of strain plotted as a function of stress as the curve crosses through zero stress, while an increased fraction of the response change is pushed out to high applied stresses. This COS spreading further slows the convergence of strain toward the saturation limit as a function of increasing stress, as compared to the magnetics model. If this trend slows convergence to saturation sufficiently in a mechanical solid, other failure mechanisms, for example, polymer chain breakage, will enter the picture before saturation stiffening of the material is evident. Thus, saturation behavior predictions of the binary transition domain theory as applied to solid mechanics may not be readily observable in all materials, due to forms of breakdown requiring a more complicated model. The standard polymer model is expected to be valid for most materials if one confines the range of applied stress to avoid more complicated breakdown mechanisms. Magnetic domains do not "break" at very high field stresses, so the breakdown limitations of the solid mechanics model do not apply to the theory as applied to magnetics.

Somewhat like the domains in solid mechanics, ferromagnetic domains in the model described here exhibit a limited range of reversible and comparatively linear compliance, since the dipole vector of a domain can be twisted out of its preferred alignment by an orthogonal H-field component, giving some permeability (above vacuum permeability) not associated with discontinuous energy transitions.

In the magnetic model, the energy barrier height appears to go down with the magnitude of the dipole moment as a function of temperature, down to the vanishing point at the Curie temperature. A direct counterpart for this magnetic scaling behavior is not recognized in the solid mechanics model. One can find an analogy between the Curie temperature in magnetics and the melting point in solid mechanics, but this analogy can be misleading. When a highly organized crystalline solid melts at a discrete temperature, for example, ice melting, this is a sharp phase transition resembling the Curie temperature transition in magnetics. Mechanical deformation with such a crystalline solid is modeled predominantly by elastic deformations of single-well domains, not binary domains. For the aspect of stress/strain relations described by binary domains, the melting process is more gradual, a progressively increasing frequency of thermally-driven strain transitions softening the material. In the magnetic model, one has a progressive increase in thermally-driven reversals of domain dipole moments for two reasons: because the excitation energy per domain is higher, varying as kT; and because the energy barrier of each domain is falling as a very nonlinear function of temperature, reaching zero at the Curie temperature. The rapid juggling of domain directions near the magnetic Curie temperature erases the memory of prior magnetization. Conversely, a permanent magnet is easily magnetized to a fairly high level by heating to the Curie temperature, subjecting it to a moderate external H-field, and cooling the material in the field. The resulting saturation is not as complete as obtained from pulsing a magnet with an extremely high H-field at room temperature, but the thermal poling process can be accomplished, for some materials, with field strengths achievable using permanent magnets to pole the heated sample (the permanent magnets must be kept cool as they are coupled magnetically to the heated material to be poled).

In the mechanical strain model, a stress field produces a strain, the stress and strain being readily distinguishable. In a magnetization model, the "stress" field, an H-field, is not readily distinguishable from the resulting "strain" field, a B-field. In a vacuum, B is given by $\mu_o H$, a simple proportion. In a magnetic material, the net B-field is the sum, $B=\mu_o H+B_i$, where $B_i$ is the intrinsic B-field attributed to polarization of the material, while the $\mu_o H$ component is the field that would exist without the "help" of the material. The intrinsic B field strength approaches an absolute saturation limit with increasing H, while the $\mu_o H$ component of the net B-field continues to climb without limit. Thus, the analog of mechanical strain in magnetics should be the intrinsic B-field, $B_i$, not the total B-field.

By analogy to the standard polymer model above, a standard magnetics model, being fairly accurate but not the most complete model, is described by seven parameters.

Standard Magnetic Model Parameters:
1) energy barrier height, mean
2) energy barrier height, dispersion
3) intrinsic energy bias, dispersion (about a zero mean)
4) strain volume magnitude, mean
5) strain volume magnitude, dispersion
6) saturation dipole moment density, aligned within a domain volume
7) Curie temperature As the solid mechanics model sometimes needs an additional linear compliance coefficient, similarly the magnetic model sometimes needs a rotational domain compliance coefficient for accuracy in certain regions, quantifying how domain orientations are twisted reversibly by an imposed H-field component orthogonal to the preferred orientation of the magnetic material within a domain or crystal. This compliance is negligible in characterizing high-permeability, low-coercive-force materials at the low H-fields in which these materials typically operate in transformers and inductors, but the compliance becomes significant at high H-fields, as illustrated in FIG. 18 by the system 1800, including a ferromagnetic sample, a data acquisition system, and means fitting to the domain model in the context of ferromagnetic domains.

Figure 18:
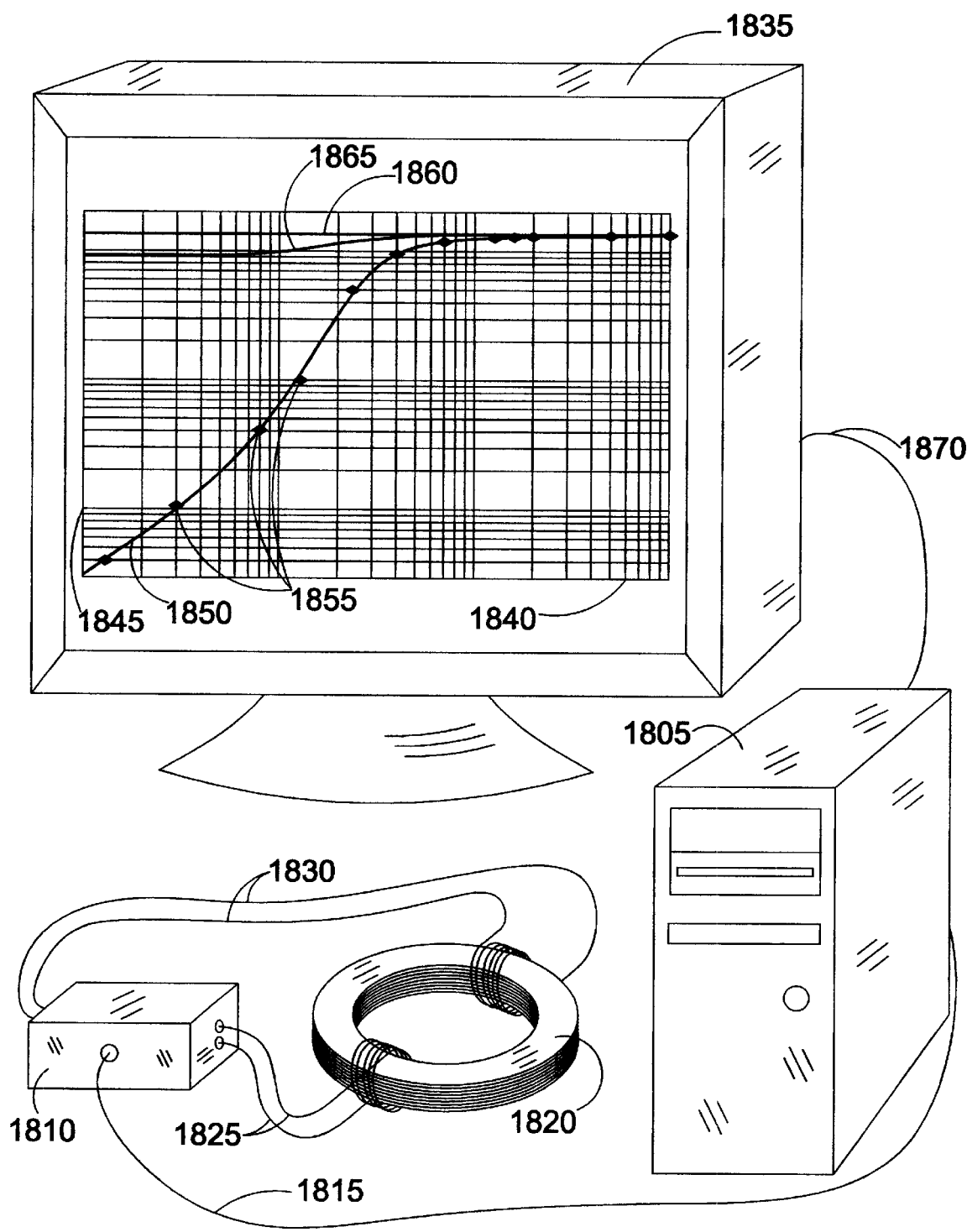
FIG. 18 illustrates testing of a ferromagnetic sample, including the apparatus and a typical response curve of flux density B versus magnetomotive field strength H, along with analytic results from a domain model.

Examining FIG. 18, computer 1805 includes a data acquisition interface card (not shown), along with appropriate software. The card mates to interface module 1810 via cable 1815, shown coming around from the back of the computer. A sample of a ferromagnetic alloy, for example, silicon transformer steel, is shown at 1820, taking the form of a torus of stacked annular laminations in the illustration. Drive wire 1825 emerges from module 1810, loops a number of times through the torus 1820 to make a drive winding, and returns to 1810, completing a circuit to a current sensing driver amplifier inside module 1810 (and not shown). Voltage sense wire 1830 similarly forms a winding around torus 1820 and connects to a voltage sensing amplifier also inside interface module 1810. The time integral of the sensed voltage indicates change in magnetic flux linking with the sense winding formed by 1830. Starting with unmagnetized iron and zero drive current, the data acquisition system (consisting of the interface card and module 1810) causes the drive current to ramp up quickly while the sense voltage is sampled and integrated, yielding data points 1855 on monitor 1835. 1870 indicates the connection from the computer to monitor 1835. The horizontal axis 1840 of the graph represents magnetic influence "stress," more commonly known as H-field strength or magnetomotive force per-unit-length around the flux path of 1820. The vertical axis 1845 represents magnetic response "strain," more commonly known as B-field strength, linked to the sense winding formed by 1830. The log—log scales of the graph reveal three decades of variation in H-field stress, clearly showing on graph 1850 the region of relatively low initial permeability (1851), the steepening of the magnetization curve as domain energy barriers are overcome (1852), the leveling off of the saturation region (1853), and a continuing B-versus-H slope in deep saturation (1854), the slope being small but well in excess of $\mu_o$, the permeability of free space. The minimum measured slope (around 1854) is associated with continuous realignment of domain directions toward the direction of the increasing H-field, as discussed above.

Curve 1850 and associated data points 1855 are from domain model computations and published data for a transformer grade steel alloy. Empirical data for the same alloy recovering from saturation were not available. It was found that widely differing combinations of three domain model parameters gave roughly equally good fits to the data points 1855, those parameters being: mean energy barrier; dispersion of the energy barrier; and dispersion of intrinsic domain energy bias about a zero mean. When the intrinsic bias dispersion was set to zero, a nearly flat return curve from saturation resembling 1860 was obtained, while a larger bias dispersion yielded a more realistic curve resembling 1865, consistent with observations that residual B-field strength (at H=0) were commonly around 70% of the saturation B-field for magnetically soft iron alloys. Nearly matching curves 1850 can be obtained for recovery curves differing as much as curves 1860 and 1865, indicating the need for data including both increasing and decreasing stress (H) in order to resolve all the significant parameters of the domain model, whether in mechanical or magnetic contexts.

With the modifications described from the solid mechanics model, this magnetics model is highly useful for the dynamic characterization of ferromagnetic and ferrimagnetic materials. One has to deal with eddy currents in ferromagnetic metals, a significant practical complication. In ferrites, where eddy currents are not sufficient to limit high frequency observations, one can observe resonant behaviors of the strain transition domains, as they commonly exhibit response peaks before a-c permeability drops sharply with further increases in frequency. Such high frequency behaviors were ignored in the description of the mechanics model given above, though they are expected if one explores frequencies sufficient to resonate the virtual particles of the microscopic domain models. It is recalled that resonances in magnetic domains are manifested as precession of magnetic vectors, rather than the mechanical model's virtual particle oscillating back and forth along a straight line in a potential well. These details of microscopic and high frequency behavior are of little consequence in characterizing bulk or macroscopic properties at moderate or low frequencies.

As with the solid mechanics model, the magnetic domain model is coupled to an error minimization method for defining best-fit model parameters from empirical data. Looking beyond the narrow context of error minimization, the model and the data-fit method together define a spectrum of testing devices and procedures, generally oriented toward exciting a magnetic material sample in complex ways at various temperatures, to bring out the details of the material's behavior. At a basic level, one still excites a sample with varying ampere-turns of an external H-field, meanwhile monitoring the change in flux through the sample by inductive measurements or using one or more Hall effect devices. The change from conventional testing comes in providing complex signals including high frequency ripples superimposed on steady or slowly varying changes in the H-field, to "exercise" various minor hysteresis loops not symmetric about H=0. Testing over a broad range of frequencies with complex waveforms is repeated over a range of temperatures to fully resolve the parameters of the binary transition domain model. With this goal accomplished, one can predict nonlinear, dissipative, saturation-limited, temperature-dependent responses of the magnetic material over a very broad range of conditions. One also gains insight into the internal microscopic behavior of the material, and insight into the processes and formulations used to prepare the material. These insights, in turn, become useful in optimizing the manufacturing process, from formulation through heat treatments and poling treatments and mechanical alignment treatments, to improve quality control and meet defined engineering needs.

Summary of Domain Methods

Figure 19:
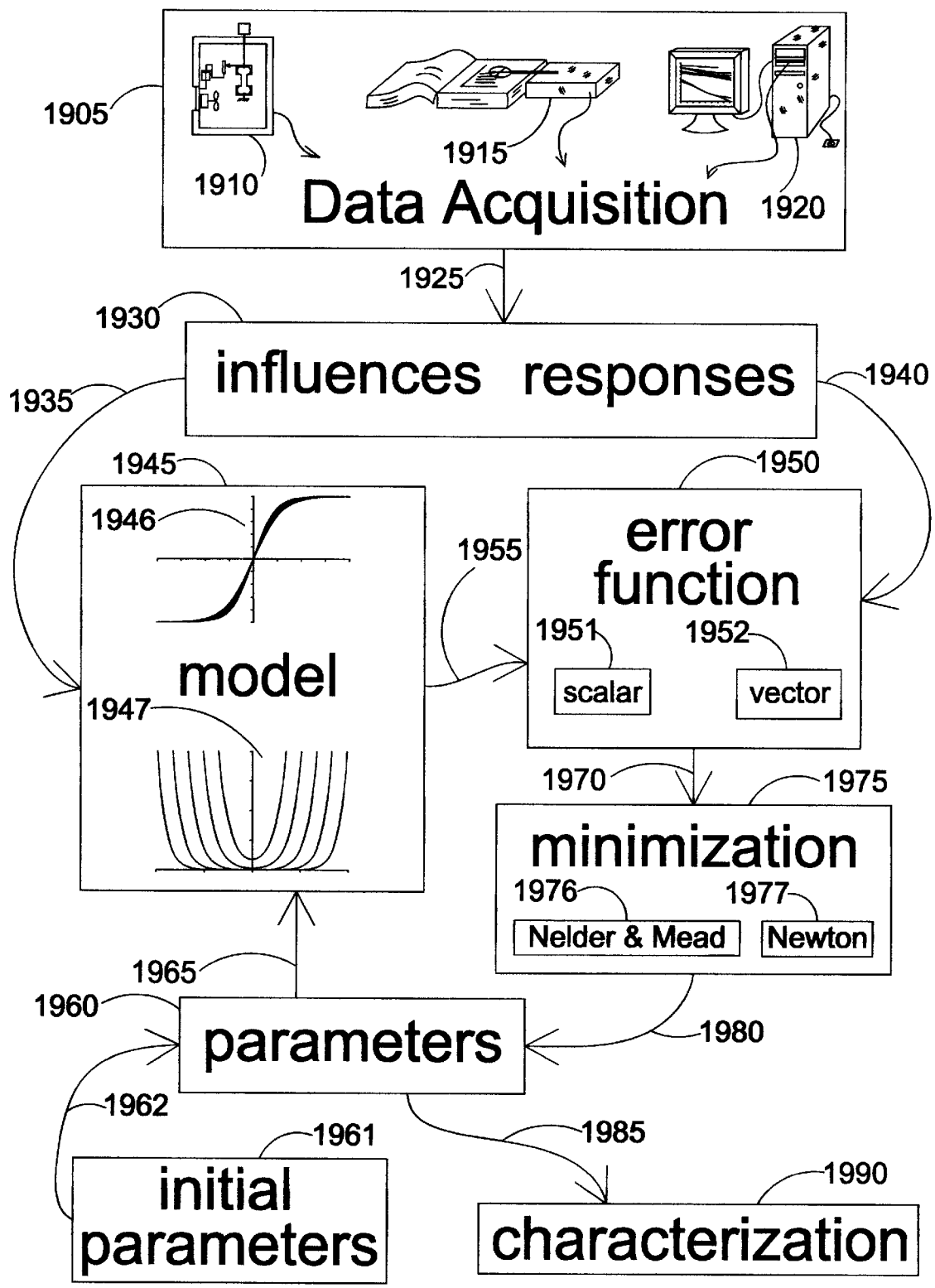
FIG. 19 is a flow diagram illustrating the process of acquiring material data, comparing those data to comparable data from a computational model, and iteratively varying the parameters of the computational model to optimize the match between the material data and the model data.

FIG. 19 summarizes the invention, combining the aspects of measurement data, mathematical modeling, and fitting the model parameters to the data in order to characterize the material. As explained in the previous section, the process of FIG. 19 applies similarly to solid mechanics and ferromagnetics. At the root of this surprising commonality is a domain model based on the statistics of energy barriers and thermal agitation, in interaction with an energy gradient or stress whose origin can be either mechanical or magnetic.

Empirical data comes into the system via 1905, some form of measurement data acquisition. The data can come from the output of a physical measurement device, here diagrammed as 1910 representing the mechanical testing device of FIG. 15, though an image representing the device of FIG. 14 would apply equally well. Data flow is indicated by the curving arrow pointing down and to the right from icon 1910.

The acquisition of empirical measurement data might be remote in time and space from the use of those data to characterize a material. That material might be a specific batch emerging from manufacture, or it might be a standard formulation such as polycarbonate, which can be produced with similar properties in any of a number of chemical plants. The data on standard materials may be derived from print format, as with the data handbook and data transfer device illustrated at 1915. A cursor with a crosshair on an instrumented arm from a measurement device is shown, the cursor being moved along the curves of printed data in a book to produce coordinate pairs and ultimately an output signal as indicated by the curving downward-pointed arrow from 1915. The printed data could also be scanned and software used, with operator guidance, to speed and automate such a process of digitizing graphical data. The needed information might be obtained from computer databases accessed through the Internet, as illustrated at 1920. A computer is shown with a cable from the back coming around the right side to a network connector, accessing the Internet. The monitor connected to the computer shows an iconic representation of the family of curves for polycarbonate from FIG. 10. Data flow is indicated by the curving arrow pointing down and to the left from 1920. The data path from 1920 could be direct, as via a data cable, or indirect, by writing the data to removable storage media for example.

The overall data output representing a material sample, whether originating from 1910 or 1915 or 1920 or some other source, travels via 1925 to 1930, a memory loaded with a data set of stored influences on a material sample and the responses resulting from those influences. The influences generally consist of a time history of instantaneous values of stress or strain or some combination thereof, plus a corresponding time history of temperature. The responses may be a corresponding time history of instantaneous values, of strain or stress, and possibly also of temperature responses that represent a departure from the ambient thermal influence. For example, a sample of rubber subjected rapidly to high strain will experience a lowered entropy and an elevated temperature as its domains are organized toward statistical saturation. This temperature elevation, measurable before thermal equilibration has gone too far, can be categorized as a response, though this response also feeds back as an influence, affecting subsequent responses in the model.

In defining what is influence and what is response, the distinction between actuation and measurement in the testing device may be ambiguous. An actuator may act primarily as a controlled force source (as with a voice coil actuator), or as a controlled mechanical displacement source (as with a stepper motor or servo motor driving a lead screw through a controlled number of rotations), or as something intermediate, characterized by a force or motion output coupled via a defined output impedance or compliance. The measurement device, for example a motion measurement or a force measurement, is ideally chosen to provide a measurement that is relatively independent of the parameter defined by the actuator, so that the actuator and measurement device together determine the values of two independent variables. Two measurement devices may better resolve force and motion, making calibration of the actuator unimportant. From the data reduced to interacting data involving stress, strain, and temperature as functions of time, the influence variables are chosen as those variables that drive the mathematical model 1945, while the response variables are chosen as the outputs of model 1945. Thus, module 1930 serves the dual function of storing data describing how a sample was "exercised," and of separating those data into influences appropriate to drive the model and responses corresponding to outputs from the model. In the model described in this Specification, stress and temperature are influences and strain is the response, but other similar formulations could differ, for example, making strain an influence and stress the response.

The influence variables go via data path 1935 to model 1945, a model based on statistical mechanics that has been discussed in detail above. As iconic representations of the model, 1946 represents the family of curves of equilibrium strain versus stress and temperature shown in FIG. 5, while 1947 represents the curves of equilibration rate versus stress and temperature shown in FIG. 6. It is recognized that the model utilizes statistical weighted sums of such equilibrium and rate functions, as illustrated (for example) in FIG. 8. The model uses the influences input via data path 1935, plus a set of initial material characterization parameters stored in memory 1960 and brought in via data path 1965, to predict responses over time. A set 1961 of initial parameters may be chosen, potentially for two purposes. First, the parameters to be used for characterizing a material may be a subset of the parameters that could be used in model 1945, in which case the choice of initial parameters 1961 defines the specific subset of parameters to represent the current material sample. Second, a reasonable first estimate of parameter values may be helpful for obtaining convergence of the error minimization process. Thus, module 1961 may be viewed as a user interface permitting a definition of the choice of parameterization, and an initial set of parameter values, to pass via data path 1962 to 1960, where parameters are stored, modified iteratively via data from path 1980, and their values passed via 1965 to model 1945. Computed responses to specified influences go out from model 1945 via data path 1955 to an error function module 1950. These model responses are compared with measured responses arriving at 1950 via data path 1940 from the stored empirical data set at 1930. The error function may be a scalar function as indicated at 1951, for example, a weighted sum of squares of differences between model-predicted strain responses and measured strain responses. Alternatively, the error function may be a vector function as indicated at 1952, possibly maintaining some separation of response measurements taken at different times or under differing circumstances, rather than lumping errors from all response measurements into a single scalar error. Of particular use is a vector error function defined, in terms of a scalar sum-of-squares error function, as the set of partial derivatives of the scalar error with respect to the components of the parameter vector from memory 1960 via data paths 1965 and 1955.

The error function 1950 feeds via data path 1970 into a mathematical minimization procedure identified at 1975. This minimization may be based on a scalar error function, for example, the Simplex Method of Nelder and Mead indicated at 1976. Alternatively, the error minimization may be based on a vector error function, for example, some variation on a matrix version of Newton's method shown as 1977.

The minimization procedure 1975 relies on a corrective feedback loop from its output 1980 back to its input 1970. This loop is provided when the output 1980 adjusts the parameters in memory 1960, which in turn feed back into model 1945 to produce new response data fed via data path 1955, into error function 1950 and via path 1970 back into minimization procedure 1975. Over multiple iterations of this loop, the minimization procedure reduces some measure of the error or overall difference between the modeled and the empirical responses. When the error minimization process is adequately converged, the resulting parameters emerge from the process via data path 1985 to define the characterization 1990 of the material in question.

Figure 20:
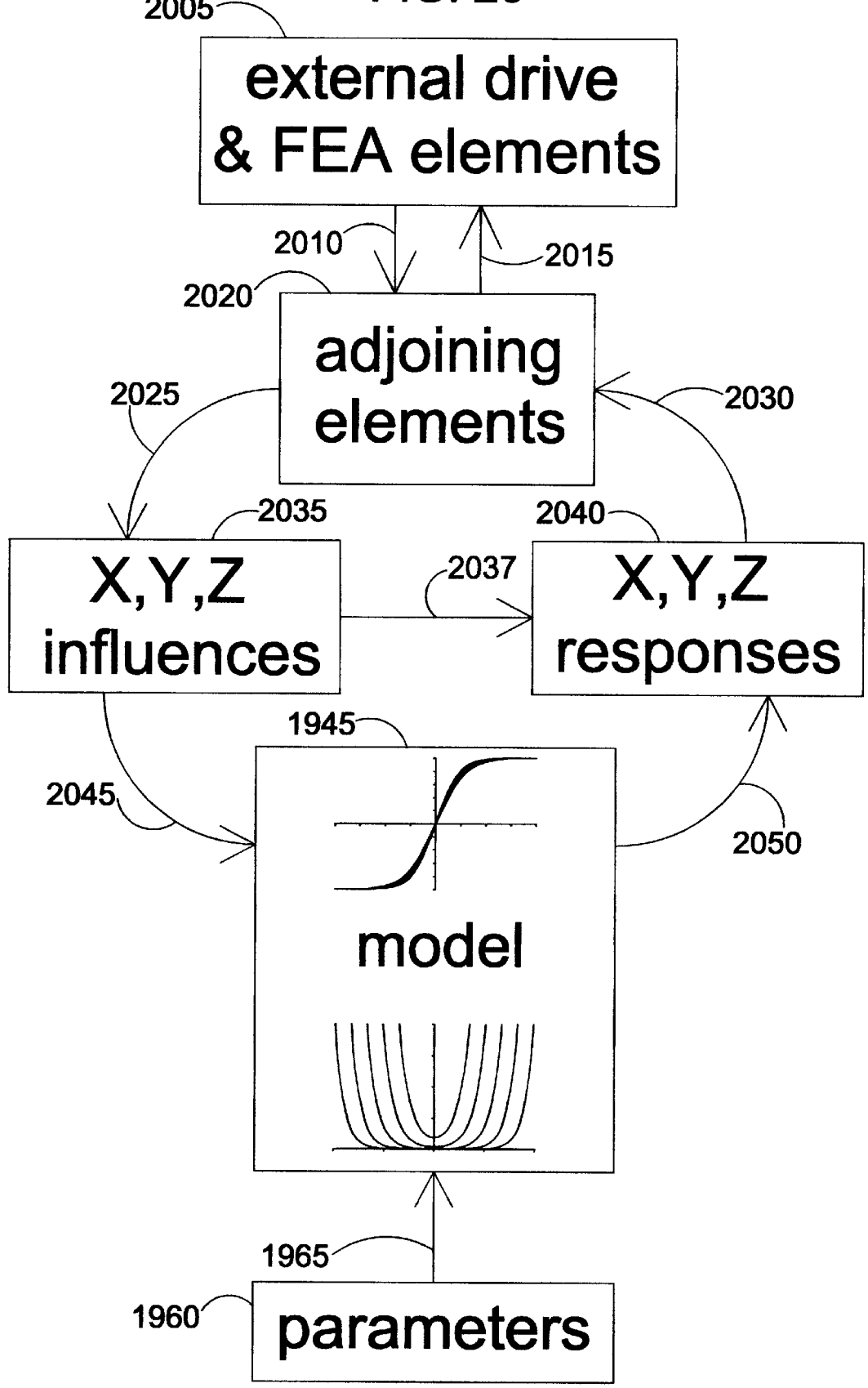
FIG. 20 is a flow diagram illustrating the spatial interconnection between a Finite Element Analysis (FEA) and a one-dimensional stress/strain model for a selected element of the FEA.

Once the materials characterization process is complete, a portion of FIG. 19 can be used for predictive modeling of the response of a material to arbitrary influences, including in a Finite Element Analysis (FEA), as illustrated in FIG. 20. An FEA will commonly involve some external driving or forcing function, influencing various elements of the model, as indicated at 2005. Because the stress/strain response of each element is treated similarly, the analysis of one single element is considered here. The parameters characterizing that element are the same parameters 1960 that resulted from convergence of the error minimization described with respect to FIG. 19. These parameters are applied to model 1945 via data path 1965, as in FIG. 19. The influences on 1945 now come via data path 2045 from 2035, while the responses feed via data path 2050 to computation module 2040, as now described.

The statuses of various FEA elements not adjoining the element in question in FIG. 20 interact with the status of intermediating adjoining elements via data paths 2010 and 2015. The stress tensors of adjoining elements stored at 2020 are resolved into force vectors acting through the interfacing facets of the chosen FEA element. The facet force vector data travel from 2020 via data path 2025 into computation module 2035, which resolves these force vectors from the various facets into an overall stress tensor acting on the chosen element. This stress tensor is decomposed into a scalar compressive stress and a tensor shear stress. The shear stress tensor is resolved into a shape, a principal axis orientation, and a shear stress magnitude. The two magnitudes, of shear stress and compressive stress, travel via data path 2045 to model 1945. If compression is considered, then the model includes a bulk modulus, which along with the compressive stress defines a compressive strain. The shear stress magnitude information drives a domain model in 1945 to define a shear strain magnitude response, varying dynamically over time. The magnitudes of shear strain and of compressive strain feed via data path 2050 to computation module 2040, while geometric shape and orientation information feeds from 2035 to 2040 via data path 2037. The geometry and orientation of stress is equated with the geometry and orientation of strain (at least in the case of isotropic substances), so that combining this geometry and orientation information with the magnitude of strain yields an overall strain tensor in 2040. This strain tensor is resolved, at each boundary facet of the chosen element, into a strain displacement vector of that facet. The facet displacement vector data feed from 2040 via data path 2030 into 2020, completing a cycle: vector forces on facets to adjoining elements, going out via 2025, are resolved into vector displacements of those same facets, coming in via 2030.

Texts on solid mechanics describe how to resolve tensors into vectors at surfaces, and also how to solve for the principal axes of tensors and the magnitudes of stress and strain associated with those principal axes. FIG. 7 illustrates the process by which magnitudes along principal axes are resolved into an angle associated with shape according to the diagram, along with a scalar magnitude associated with that shape or associated diagram angle. FIG. 20, combined with the description above, indicates how these transformations involving tensors, vectors, shapes, orientations, and magnitudes, permit elements of an FEA to be interfaced to one-dimensional element models, including a dynamic domain model and possibly an algebraic model of compression and expansion. Solutions to this FEA problem call for non-trivial simultaneous solutions for the responses of the interacting elements, but the nature of such simultaneous systems of equations, and approaches to their solution, are understood. The core difference between the present analysis and conventional FEA comes in modeling the temperature-dependent, dynamic, nonlinear responses of elements in shear.

The domain analysis provided here is based on a fixed tensor shape and orientation associated with the one-dimensional domain model. In an FEA analysis, an initial linear perturbation model may be used to define the shapes and orientations of vector/tensor interactions. If small changes in shapes and orientations of shear stress arise during the analysis, those aspects of the FEA can be updated progressively. The model works under these conditions.

The model may not be accurate under extreme changes in stress orientation and shape, for example, where stress initially acts entirely in a horizontal plane and later comes to act in a vertical plane. The stress/strain history carried by the arrayed dynamic strain variables ($S_{ijk}$) when stress has acted in the initial orientation are not be expected to apply properly when stress comes to operate in an entirely new direction. The present invention, viewed as a tool for characterization and analytic extrapolation of material properties and responses, is trustworthy only when the boundaries of its application are well defined. The above statements concerning large changes in stress orientation and shape, along with earlier statements about inapplicability of the model (in its present form) to fatigue and to the extremities where polymer molecules break, define a broad but finite confidence boundary, within which the user will find a powerful and reliable tool. The future will see improvements in handling, simplifying, and approximating the many computations required to implement this improved, dynamic analysis, particularly as applied to large numbers of elements of a dynamic FEA, leading to greater speed and utility of a tool that is already well defined by this Specification. The payoff of such improvements will be in bringing very realistic FEA from the realm of supercomputers to the realm of workstations and desktop computing, leading to much better prediction and understanding of time-dependent stress, strain, and of failure conditions in systems such as elastomer balloon infusion pumps, flexing plastic hinges, crash helmets and bumpers subject to impact at high and low temperatures, and rubber and plastic o-rings subjected to high preset loads, high pressure loads, and large deformations, to name a few. While inexpensive FEA applications await computational refinements, the invention as applied to single elements or test samples will find immediate practical use in materials testing, characterization, inspection, feedback for process control, and for deeper understanding and intuitive grasp of material properties, as developed through use of and familiarity with the models, methods, and tools taught here.

In all embodiments, the goal is to derive a statistical mathematical model, characterized by a concise set of governing parameters, which may subsequently be used to predict the nonlinear, dynamic, temperature-dependent behavior of the tested material under widely varying conditions and influences.

I claim:

1. A method for quantifying and characterizing the properties of a material from a sample of said material, comprising the steps of:
    (a) measuring responses of said sample to a range of applied influences;
    (b) computing from said responses and said applied influences a concise set of parameters of a statistical mathematical model which most closely matches mathematical responses of said model to said responses of said sample, and
    (c) deriving a dynamic simulation model of said material whose characteristics are closely representative of said material,
whereby said dynamic simulation model enables the characterization of said material both within and beyond said range of applied influences.

2. The method of claim 1 wherein said step of measuring responses of said sample to a range of applied influences comprises:
    (a) providing said sample with measuring means;
    (b) providing a means for imposing known applied influences upon said sample;
    (c) imposing said applied influences upon said sample, and
    (d) measuring the effects of said known applied influences upon said sample.

3. The method of claim 2 wherein at least one of said known applied influences is temperature.

4. The method of claim 1 wherein said step of measuring responses comprises:
    means for reading and storing previous response data drawn from pre-existing measurements of an earlier sample of said material as said earlier sample had earlier responded to a range of applied influences,
whereby said pre-existing measurements, for example in printed form, are directly used in said method in lieu of at least some measurement trials.

5. The method of claim 1 wherein said step of computing a concise set of parameters comprises:
    (a) numerically recording instantaneous values of said applied influences and the corresponding instantaneous values of said responses of said sample;
    (b) applying a functional minimization procedure to parameters of a said dynamic simulation model to minimize an error function of differences between mathematical responses of said dynamic simulation model and physical said responses of said sample to said applied influences,
whereby arbitrary numerical inputs to said dynamic simulation model, analogous to arbitrary numerical values of applied influences, create numerical outputs analogous to numerical values of responses of said sample, and
whereby responses of said sample can be interpolated and extrapolated for values of applied influences which lie between and beyond said recorded instantaneous values thereof.

6. The method of claim 1 wherein said statistical mathematical model is a predictive dynamic simulation model that includes statistical material strain transition domains, said domains being characterized by two or more adjacent potential wells seriatim each having an unique minimum energy potential and separated from adjacent potential wells by a corresponding transition energy barrier confining a virtual particle exclusively within one of said two or more adjacent potential wells, restoring said virtual particle toward said minimum energy potential of that said potential well in which it is confined, yet permitting said virtual particle to transition between said adjacent potential wells if said virtual particle attains an energy greater in value than that of said corresponding transition energy barrier, whereby said virtual particle attains said energy greater in value through a combination of thermal energy and coupling to an external mechanical stress, and whereby non-linear, visco-elastic and viscous liquid phase material properties can be modeled.

7. A system for quantifying and characterizing the properties of a material from at least one sample of said material, comprising:

(a) at least one means for imposing known applied influences upon said at least one sample;

(b) at least one means for measuring responses of said at least one sample to said applied influences;

(c) means for recording and storing instantaneous values of said known applied influences and of said responses;

(d) a statistical mathematical model comprising parameters for matching said model to said instantaneous values of said applied influences and of said responses;

(e) means for computing from said instantaneous values a concise set of said parameters which closely matches mathematical responses of said model to physical said responses of said sample to said applied influences, and (f) deriving a dynamic simulation model of said material whose characteristics are representative of said material, whereby said dynamic simulation model enables the characterization of said material both within and beyond said range of applied influences.

8. The system of claim 7 wherein said means for imposing said known applied influences comprises means for imposing known forces abruptly.

9. The system of claim 8 wherein said means for imposing known forces abruptly further comprises an engagement mechanism which imposes tension upon said sample, but which decouples so as not to impose compression thereupon, whereby said tension increases abruptly from a minimal value to a predetermined value, and whereby compressive forces are not imposed upon said sample, thereby preventing buckling or other compressive damage thereto.

10. The system of claim 9 wherein said engagement mechanism comprises at least one spring of a predetermined strength, whereby engagement of said mechanism abruptly imposes said predetermined value of tension upon said sample.

11. The system of claim 7 wherein said parameters comprise information about:

(a) an increase in strain equilibration rate as a function of increasing stress;

(b) an increase in strain equilibration rate as a function of increasing temperature; and (c) a decreasing rate of change of equilibrium strain with respect to stress as a function of increasing stress over a range of stresses.

12. The system of claim 11 wherein said parameters further comprise information about a decrease in equilibrium strain as a function of increasing temperature at constant stress.

13. A method of material characterization and predictive computational modeling of mechanical stress and strain at varying temperatures, said characterization and said modeling based on a statistical strain transition domain model and employing steps of determining, in said model, statistical parameters comprising at least four selected from the group consisting of:

(a) energy barrier height, mean;

(b) energy barrier height, dispersion;

(c) intrinsic energy bias, dispersion (about a zero mean);

(d) strain volume magnitude, mean;

(e) strain volume magnitude, dispersion; and (f) total domain density.

14. The method of claim 13 further comprising the steps of:

(a) determining by measurement time-varying stress and strain of a material sample at varying temperatures;

(b) determining by computation similar time-varying stress and strain, based on the numerical values of said varying temperatures and based on said statistical strain transition domain model;

(c) in multiple steps of said determining by computation, varying said statistical parameters to find a set of values thereof which lead to a best-fit match between said determining by measurement and said determining by computation; and (d) characterizing said sample by said set of values of said statistical parameters.

15. The method of claim 14, further comprising the step of predicting dynamic behavior of a finite element of said material, over time and at specified temperatures over time, within the constraints of a computational finite element analysis.

* * * * *